(12) United States Patent
Pan et al.

(10) Patent No.: US 7,169,817 B2
(45) Date of Patent: Jan. 30, 2007

(54) BIS-AROMATIC ALKANOLS

(75) Inventors: Shifeng Pan, San Diego, CA (US); Nathanael S. Gray, La Jolla, CA (US); Wenqui Gao, San Diego, CA (US); Klaus Hinterding, Ruemmingen (DE); Sophie Lefebvre, San Diego, CA (US); Yuan Mi, San Diego, CA (US); Peter Nussbaumer, Enzerdorf (AT); Wei Wang, San Diego, CA (US); Federic Zecri, Uffheim (FR); Fan Yi, Poway, CA (US); Lawrence Blas Perez, Hakettstown, NJ (US); Kenneth Richad la Montagne, Morristown, NJ (US); Peter Ettmayer, Vienna (AT)

(73) Assignee: IRM LLC, Hamilton (BM)

(*) Notice: Subject to any disclaimer, the term of this patent is extended or adjusted under 35 U.S.C. 154(b) by 25 days.

(21) Appl. No.: 10/445,967

(22) Filed: May 27, 2003

(65) Prior Publication Data
US 2004/0048857 A1    Mar. 11, 2004

Related U.S. Application Data

(60) Provisional application No. 60/432,704, filed on Dec. 10, 2002.

(30) Foreign Application Priority Data

May 27, 2002    (GB) ................... 0212210.9
Nov. 14, 2002   (GB) ................... 0226624.5

(51) Int. Cl.
| C07C 211/03 | (2006.01) |
| C07C 251/32 | (2006.01) |
| A61K 31/15  | (2006.01) |
| A61K 31/137 | (2006.01) |

(52) U.S. Cl. .................. 514/650; 564/15; 564/265; 564/337; 514/640

(58) Field of Classification Search ............. 564/15, 564/337, 265; 514/650, 640
See application file for complete search history.

(56) References Cited

FOREIGN PATENT DOCUMENTS

EP    627406 A1    12/1994
EP    778263 A1    6/1997

OTHER PUBLICATIONS

Sarah Spiegel (BIOMOL, Research News, Apr. 2000, vol. 9 No. 1, pp. 1-15).*
Timothy Hia, Seminars in Cell & Developmental Biology 15 (2004) 513-520.*
Adachi, Kunitomo et al., Bioorganic and Medicinal Chemistry Letters, vol. 5, No. 8, pp. 853-856 (1995); Design, Synthesis, and Structure-Activity Relationships of 2-Substituted-2-Amino-1-3-Propanediols: Discoverty of a Novel Immunosuppressant, FTY720.

* cited by examiner

*Primary Examiner*—Kahsay Habte
(74) *Attorney, Agent, or Firm*—Scott W. Reid; The Genomics Institute of the Novartis Research Found

(57) ABSTRACT

The present invention relates to biphenylyl derivatives, processes for their production, their uses and pharmaceutical compositions containing them. Compounds according to the present invention are based upon the chemical formula:

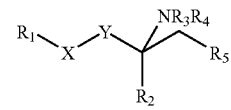

wherein the substituents have the values mentioned herein.

7 Claims, No Drawings

BIS-AROMATIC ALKANOLS

CROSS-REFERENCE TO RELATED APPLICATIONS

This application claims the benefit of priority to U.S. Provisional Patent Application No. 60/432,704 (filed Dec. 10, 2002), U.K. patent application Number 0226624.5 (filed Nov. 14, 2002) and U.K. patent application Number 0212210.9 (filed May 27, 2002). The full disclosures of these applications are incorporated herein by reference in their entirety and for all purposes.

BACKGROUND

1. Field of the Invention

The present invention relates to biphenylyl derivatives, processes for their production, their uses and pharmaceutical compositions containing them.

2. Background

EDG receptors belong to a family of closely related, lipid activated G-protein coupled receptors. Edg1, Edg3, Edg5, Edg6, and Edg8 (also respectively termed S1P1, S1P3, S1P2, S1P4, and S1P5) are identified as receptors specific for sphingosine-1-phosphate (S1P). Edg2, Edg4, and Edg7 (also termed LPA1, LPA2, and LPA3, respectively) are receptors specific for lysophosphatidic (LPA). Among the S1P receptor isotypes, Edg1, Edg3 and Edg5 are widely expressed in various tissues, whereas the expression of Edg6 is confined largely to lymphoid tissues and platelets, and that of Edg8 to the central nervous system. EDG receptors are responsible for signal transduction and are thought to play an important role in cell processes involving cell development, proliferation, maintenance, migration, differentiation, plasticity and apoptosis. Certain EDG receptors are associated with diseases mediated by lymphocyte interactions, for example, in transplantation rejection, autoimmune diseases, inflammatory diseases, infectious diseases and cancer. An alteration in EDG receptor activity contributes to the pathology and/or symptomology of these diseases. Accordingly, molecules that themselves alter the activity of EDG receptors are useful as therapeutic agents in the treatment of such diseases.

SUMMARY OF THE INVENTION

The present invention relates to biphenylyl derivatives, processes for their production, their uses and pharmaceutical compositions containing them.

More particularly the present invention provides a compound of formula I

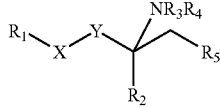

wherein

Y is —$CH_2CH_2$—, —$CH_2CH(OH)$—, —$CH(OH)CH_2$—, —$C(O)CH_2$—, —$CH_2C(O)$—, —CH=CH—; or 1,2-cyclopropylene;

X is arylene or $C_{5-6}$heteroarylene optionally substituted by one to three substituents selected from halogen, nitro, $C_{1-10}$alkyl and halogen-substituted $C_{1-6}$alkyl;

$R_1$ is aryl, aryl-$C_{2-4}$alkenyl, heteroaryl, or heteroaryl-$C_{2-4}$alkenyl each being substituted by (i) one to three substituents selected from hydrogen, halogen, amino, phenyl, heteroaryl, heteroaryl-$C_{1-4}$alkyl, $C_{1-10}$alkyl, cycloalkyl-$C_{1-4}$alkyl, cycloalkyl-$C_{1-4}$alkoxy, $C_{1-10}$alkoxy, $C_{2-10}$alkenyl, $C_{2-10}$alkynyl, $C_{1-10}$alkylthio, $C_{1-10}$alkylsulfonyl, $C_{1-10}$alkylsulfinyl, $C_{1-4}$alkyl-$S(O)_2NH$—, phenyl$C_{1-6}$alkyl, or phenyl$C_{1-6}$alkoxy, in each of which any aliphatic part of the group may be straight or branched chain and optionally substituted by up to three substituents selected from halogen, amino, hydroxy, cyano, or cycloalkyl groups and optionally interrupted by a double or triple bond or one or more C(O), $NR_{12}$, S, S(O), $S(O)_2$ or O groups, wherein $R_{12}$ is hydrogen or $C_{1-6}$alkyl; and any aromatic group may be optionally substituted by one to three substituents selected from halogen, cyano, amino, $C_{1-4}$alkyl halogen-substituted-$C_{1-4}$alkyl and $C_{1-8}$alkoxy; and/or (ii) a group of formula (a), (b), (c), (d), (e), (f) or (g):

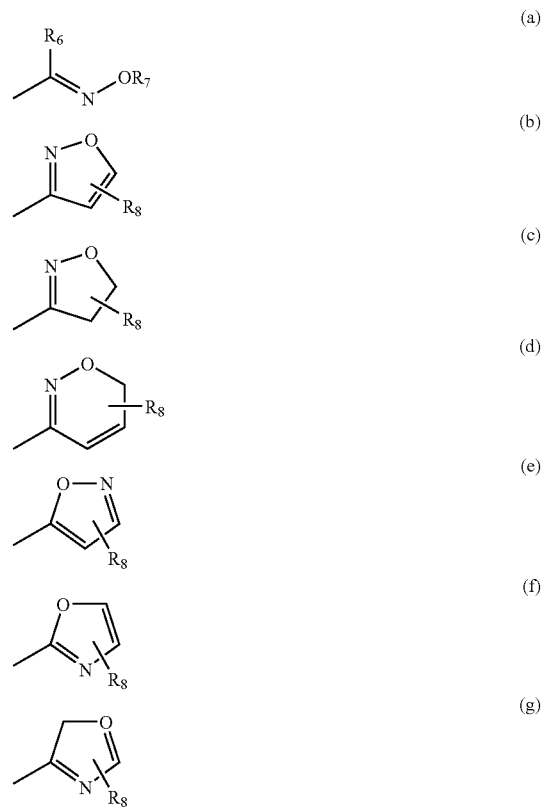

in which each of $R_6$, $R_7$ and $R_8$ independently, is hydrogen; phenyl, $C_{1-10}$alkyl, cycloalkyl, heteroaryl, heteroaryl-$C_{1-4}$alkyl, $C_{1-10}$alkoxy, $C_{2-10}$alkenyl, $C_{2-10}$alkynyl, $C_{1-10}$alkylthio, $C_{1-10}$alkylsulfonyl, $C_{1-10}$alkylsulfinyl, phenyl$C_{1-8}$alkyl, or phenyl$C_{1-6}$alkoxy, in each of which any aliphatic part of the group may be straight chain or branched and may be optionally substituted by up to three halogen, hydroxy, cycloalkyl, or $C_{1-4}$alkoxy groups and optionally interrupted by a double or triple bond or one or more C(O), $NR_{12}$, S, S(O), $S(O)_2$ or O groups, and any aromatic group may be optionally substituted by one to three substituents selected from halogen, $CF_3$, $C_{1-8}$alkyl and $C_{1-8}$alkoxy;

$R_2$ is hydrogen; halogen; $C_{1-4}$alkyl optionally substituted with one or more halogens; $C_{2-6}$ alkenyl; $C_{2-6}$alkynyl;

cycloalkyl optionally substituted by halogen; aryl optionally substituted with hydroxy; or $C_{1-4}$alkyl optionally substituted on the terminal C atom by OH or a residue of formula (h):

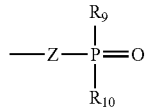

(h)

in which Z is a direct bond, O, S, $(CH_2)_{1-2}$, $CF_2$, or $NR_{11}$ where $R_{11}$ is H, $(C_{1-4})$alkyl or halogen-substituted $(C_{1-4})$ alkyl; and each of $R_9$ and $R_{10}$, independently, is H, OH, $(C_{1-4})$alkyl optionally substituted by one to three halogens, or $(C_{1-4})$alkoxy optionally substituted by halogen; with the proviso that $R_9$ and $R_{10}$ are not both hydrogen;

each of $R_3$ and $R_4$, independently, is H or $C_{1-4}$alkyl optionally substituted by halogen or acyl; and $R_5$ is H, —OH, —Oacyl, —NHacyl, or a residue of formula (h) as defined above;

provided that at least either $R_2$ comprises a terminal OH or a residue of formula (h) or $R_5$ is OH or a residue of formula (h), or a salt thereof.

DETAILED DESCRIPTION OF THE INVENTION

The invention provides compounds that are useful in the treatment and/or prevention of diseases or disorders mediated by lymphocyte interactions. Also provided are methods for treating such diseases or disorders. Compounds of formula I are also useful in cancer chemotherapy.

Alkyl as a group and as a structural element of other groups, e.g. halogen-substituted-alkyl, alkoxy, acyl, alkylthio, alkylsulfonyl and alkylsulfinyl, may be straight or branched chain, e.g. methyl, ethyl, propyl, iso-propyl or butyl. Alkenyl as a group and as a structural element of other groups contains one or more carbon-carbon double bonds and may be e.g. vinyl. Any double bonds may be in the cis- or trans-configuration. Alkynyl as a group and as a structural element of other groups and compounds contains at least one carbon—carbon triple bond and may also contain one or more C═C double bonds, and may be e.g. propyn-2-yl. Alkyl, alkenyl, alkynyl or cycloalkyl substituted by halogen, e.g. as $R_2$, may be alkyl, alkenyl, alkynyl or cycloalkyl wherein one or more H are replaced by halogen, e.g. Cl or F, e.g. $CHCl—CH_3$ or $CF_3$; halogen-substituted alkyl, alkenyl, alkynyl or cycloalkyl may be partially halogenated or perhalogenated, whereby in the case of multiple halogenation, the halogen substituents may be identical or different.

Any cycloalkyl group, alone or as a structural element of other groups may contain from 3 to 8 carbon atoms, e.g. from 3 to 7 carbon atoms, preferably from 3 to 6 carbon atoms.

Acyl may be a residue R—CO wherein R is $C_{1-6}$alkyl, $C_{3-6}$cycloalkyl, phenyl or phenyl$C_{1-4}$alkyl.

Halogen may be F, Cl or Br, preferably F or Cl.

Aryl means a monocyclic or fused bicyclic aromatic ring assembly, e.g. containing six to ten ring carbon atoms. For example aryl may be naphthyl, phenyl, or phenyl optionally substituted, preferably a residue of formula (k):

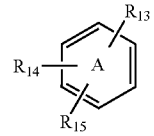

(k)

wherein each of $R_{13}$, $R_{14}$ and $R_{15}$, independently, is H; halogen; $C_{1-8}$alkyl optionally substituted by one or more halogen, hydroxy, or $C_{1-4}$alkoxy or optionally interrupted by one oxy or by one or more oxygen atoms; $C_{1-8}$alkoxy; $C_{2-8}$alkenyl; $C_{2-8}$alkynyl; $C_{1-8}$alkylthio; $C_{1-8}$alkylsulfonyl; $C_{1-8}$alkylsulfinyl; phenyl$C_{1-6}$alkyl; phenyl$C_{1-6}$alkoxy; phenyl optionally substituted by halogen, $CF_3$, $C_{1-4}$alkyl and/or $C_{1-4}$alkoxy. When ring A is monosubstituted, the substitutent is preferably in the para position.

Arylene means a divalent radical derived from an aryl group. For example arylene as used in this application may be phenylene or naphthylene, preferably phenylene, more preferably 1,4-phenylene.

Aryl-$C_{2-4}$alkenyl may be e.g. styryl.

Heteroaryl means aryl, as defined in this application, optionally substituted, provided that one or more of the ring carbon atoms indicated are replaced by a heteroatom, e.g. 1 to 3 heteroatoms, selected from N, O or S, and, e.g. each ring is comprised of 5 to 9 ring atoms. Examples include thienyl, pyridinyl, isoxazolyl, benzoxazolyl, benzo[1,3]dioxolyl, furyl, pyrrolyl, benzothienyl, benzofuryl, indolyl or benzoxadiazolyl, preferably thienyl or pyridinyl. Suitable substitutents are e.g. methyl, halogen or formyl. When substituted, it is preferably monosubstituted. Heteroarylene means heteroaryl, as defined in this application, provided that the ring assembly comprises a divalent radical.

Compounds of the present invention are often active with free hydroxy and free amine groups. Forms of the compound that have the hydroxy or amine group present in a protected form often function as prodrugs. Prodrugs are compounds that are converted into an active drug form after administration, through one or more chemical or biochemical transformations. Forms of the compounds of the present invention that are readily converted into the claimed compound under physiological conditions are prodrugs of the claimed compounds and are within the scope of the present invention. Examples of prodrugs include forms where a hydroxy group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes. Some molecules of the present invention may themselves be prodrugs, such as those comprising a phosphate residue of formula (h) which may be enzymatically dephosphorylated to a hydroxy group. Alternatively, a compound of the invention wherein $R_2$ and/or $R_5$ comprises a free hydroxy group may be enzymatically phosphorylated to a compound comprising a phosphate residue of formula (h). The present invention also includes both the enzymatically phosphorylated or dephosphorylated compounds of formula I, optionally in equilibrium.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts; when group (h) is present and $R_9$ or $R_{10}$ is —OH, group (h) may also be present in salt form, e.g. an ammonium salt or salts with metals such as sodium, potassium, calcium, zinc or magnesium, or a mixture thereof. Compounds of formula I and their salts in hydrate or solvate form are also part of the invention.

When the compounds of formula I have asymmetric centers in the molecule, various optical isomers are obtained. The present invention also encompasses enantiomers, racemates, diastereoisomers and mixtures thereof. For example the central carbon atom bearing $R_2$, $CH_2$—$R_5$ and $NR_3R_4$ may have the R or S configuration. Compounds having the R configuration at this central carbon atom are preferred. Moreover, when the compounds of formula I include geometric isomers, the present invention embraces cis-compounds, trans-compounds and mixtures thereof. Similar considerations apply in relation to starting materials exhibiting asymmetric carbon atoms or unsaturated bonds as mentioned above.

In the compounds of formula (I), the following significances are preferred individually or in any sub-combination:

1. Y is —$CH_2$—$CH_2$— or —CH(OH)—$CH_2$—, preferably —$CH_2$—$CH_2$—;

2. X is 1,4-phenylene;

3. $R_1$ is mono- or di-substituted phenyl or thienyl, preferably para-monosubstituted phenyl, e.g. substituted by a group $R_{15}$, as defined below; e.g. $R_1$ is a group of formula (k)

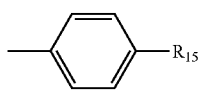

(k)

where $R_{15}$ is straight chain $C_{5-8}$alkyl; $C_{2-8}$alkenyl; or straight chain or branched $C_{1-8}$alkoxy optionally substituted by one $C_{3-6}$cycloalkyl or by a phenyl group optionally substituted by up to three halogens;

4. $R_1$ is mono- or di-substituted phenyl or thienyl, preferably para-monosubstituted phenyl, e.g. substituted by a group of formula (a), (b) or (c) as defined above;

5. $R_1$ is phenyl monosubstituted by a group of formula (a), preferably in the trans configuration;

6. In the group of formula (a), $R_6$ is $C_{1-6}$alkyl or $C_{3-6}$cycloalkyl, preferably straight chain $C_{1-4}$alkyl, cyclopropyl or cyclopropylmethyl;

7. In the group of formula (a), $R_7$ is H, $C_{1-6}$alkyl, $C_{2-6}$alkenyl, or $C_{2-6}$alkynyl, preferably straight chain $C_{1-6}$alkyl, vinyl, allyl or propyn-2-yl;

8. $R_2$ is $C_{1-4}$alkyl optionally substituted on the terminal C atom by OH or a residue of formula (h), preferably $R_2$ is methyl or hydroxymethyl, more preferably hydroxymethyl;

9. At least one of $R_3$ and $R_4$ is hydrogen, preferably both are hydrogen;

10. $R_5$ is hydrogen, —OH, —NHC(O)$C_{1-4}$alkyl or a residue of formula (h);

11. Each of $R_9$ and $R_{10}$ is —OH;

12. Z is O.

The present invention also includes a process for the preparation of a compound of formula I which process comprises removing the hydrolysable groups present in a compound of formula II

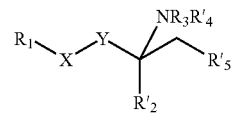

II wherein X, Y, $R_1$ and $R_3$ are as defined above, $R_4'$ is an amino protecting group, $R_2'$ has one of the significances given for $R_2$ above except that the terminal OH when present in the OH-substituted $C_{1-4}$alkyl is in protected form or the residue of formula (h) is replaced by a residue of formula (h') and $R_5'$ is $R_5''$ in which $R_5''$ is H, —OH in protected form or a residue of formula (h'), provided that at least one of $R_2'$ and $R_5'$ is OH in protected form or a residue of formula (h'), the residue of formula (h') being:

(h')

wherein Z is as described above, and each of $R_9'$ and $R_{10}'$ is a hydrolysable group and, where required, converting the compounds of formula I obtained in free form into the desired salt form, or vice versa.

The process may be carried out in accordance with methods known in the art. Hydrolysable groups may be hydroxy and amino protecting groups, e.g. when compounds of formula I are free of a residue of formula (h), and/or groups such as $R'_9$ and $R'_{10}$. Examples of protecting groups for hydroxy and amino groups are, e.g. as disclosed in "Protective Groups in Organic Synthesis" T. W. Greene, J. Wiley & Sons NY, $2^{nd}$ ed., chapter 7, 1991, and references therein, e.g. benzyl, p-methoxybenzyl, methoxymethyl, tetrahydropyranyl, trialkylsilyl, acyl, tert-butoxy-carbonyl, benzyloxy-carbonyl, 9-fluorenylmethoxycarbonyl, trifluoroacetyl, trimethylsilyl-ethanesulfonyl and the like.

Preferably $R_9'$ and $R_{10}'$ are identical and have the significance of, e.g. phenoxy or benzoxy or form together a cyclic system such as in 1,5-dihydro-2,4,3-benzodioxaphosphepin.

The removal of the hydroxy and amino protecting groups and/or of $R'_4$ or $R'_5$ groups in the compounds of formula II may conveniently be performed according to methods known in the art, e.g. by hydrolysis, e.g. in a basic medium, e.g. using a hydroxide such as barium hydroxide. It may also be performed by hydrogenolysis, e.g. in the presence of Pearlman's catalyst, e.g. as disclosed in J. Org. Chem., 1998, 63, 2375–2377. When the compounds of formula II are free of a residue of formula (h'), the removal of the hydroxy and amino protecting groups may also be performed in an acidic medium.

Compounds of formula II, used as starting materials, and salts thereof are also novel and form part of the invention.

The present invention also includes a process for the preparation of a compound of formula II which process comprises coupling a compound of formula III:

$R_1$—Q III wherein $R_1$ is as defined above, Q is boron, silicon, magnesium, tin, lithium, copper or zinc, where each of these elements is bound to one or more suitable ligands, e.g. hydroxy, $C_{1-8}$alkoxy, $C_{1-8}$alkyl optionally substituted by a terminal carboxyl group, halogen or pseudohalogen, e.g. triflate (trifluoromethylsulfonate), mesylate, tosylate or cyanide; with a compound of formula IV:

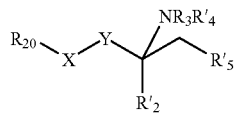

IV wherein X, Y, R'$_2$, R$_3$, R'$_4$ and R'$_5$ are as specified above, and R$_{20}$ is halogen, preferably Cl, Br, I, triflate, tosylate or mesylate;

under the catalysis of a transition metal or salt thereof, e.g. palladium, rhodium or platinum, e.g. in the presence of a suitable ligand, e.g. a phosphine, carboxylate or heterocyclic carbene.

Compounds of formula II wherein R'$_5$ is a residue of formula (h') may also be prepared by reacting a compound of formula II wherein R'$_5$ is hydroxy in protected or unprotected form, with a corresponding phosphorylating agent, e.g. a phosphorochloridate, e.g. diphenylchlorophosphate or dibenzylchlorophosphate, cyanoethylphosphate, a phosphoramidate such as N-phenyl phosphoramidate, 3-(diethylamino)-1,5-dihydro-2,4,3-benzodioxaphosphepin and the like.

Many compounds of the present invention, having general structure of Formula I, may be synthesized from protected aminomalonate esters such as ii (Scheme I). This compound may be readily alkylated by alkylating agents such as iii (wherein Y' is CH$_2$, CH(OH) or C=O) having leaving groups (—Q) such as bromide, iodide, or an alkyl or aryl sulfonate ester. These alkylating agents and methods for their preparation are generally well known in the art. The products of these alkylations are compounds such as iv, which may be reduced to produce compounds v of the present invention. This approach enables synthesis of compounds v, having various X—R$_1$ groups and linking groups between X and the amino-propanediol.

Compounds such as v may be used to prepare other compounds of the present invention, using well known protection strategies (Scheme I) to differentiate the two hydroxy groups. For example, v may be protected as an oxazoline (vi), leaving one hydroxy group free for further functionalization. Methods well known in the art (alkylation, acylation, oxidation, reduction, and combinations of these steps) may be used to convert the CH$_2$OH group of compound vi into various R$_2$ groups to provide other compounds that are within the scope of the present invention such as vii and viii.

Alternatively, a compound of formula ix may be protected by acylation, for example, allowing functionalization of the aryl group (Scheme II, wherein Y', R$_6$ and R$_7$ are as described above). When the aryl group is a phenyl, as shown for example with ix, it may be acylated to produce a compound x that may undergo Friedel-Crafts acylation under conventional conditions to produce a compound such as xi. This acylated compound may then be further transformed into compounds such as xii(a), xii(b), xii(c) and xii(d) by procedures well known to those of skill in the art. For example, conversion to an oxime (xii(a)) is accomplished by treatment with an alkoxyamine as described below for Example 5. Reduction to the alcohol xii(b) may be accomplished with sodium borohydride, for example; further reduction to remove the hydroxy group (producing xii(c)) may be achieved with catalytic hydrogenation or with triethylsilane and trifluoroacetic acid. Olefination to form xii(d) may be achieved with Wittig or Horner-Emmons conditions, via Petersen olefination, or by a Grignard addition followed by elimination of the benzylic alcohol. Such transformations enable the incorporation of diverse substituents on the aryl groups of the compounds of the present invention.

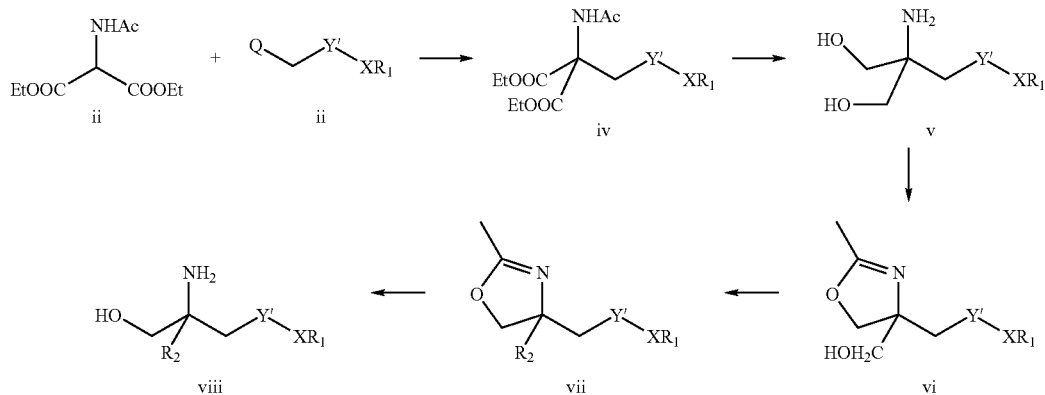

Scheme I

Scheme II

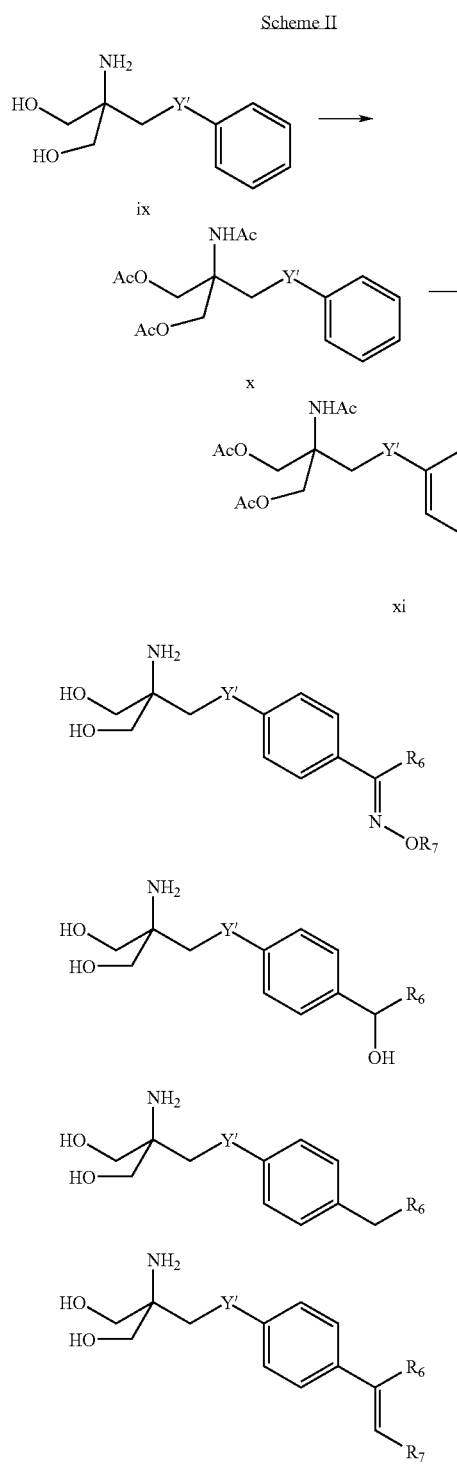

acyl azide, for example, which may be used to prepare compounds xix. Reduction of the ester group then provides compounds xix of the present invention. This enables access to compounds wherein $R_2$ is an aryl group such as e.g. 2-hydroxyphenyl.

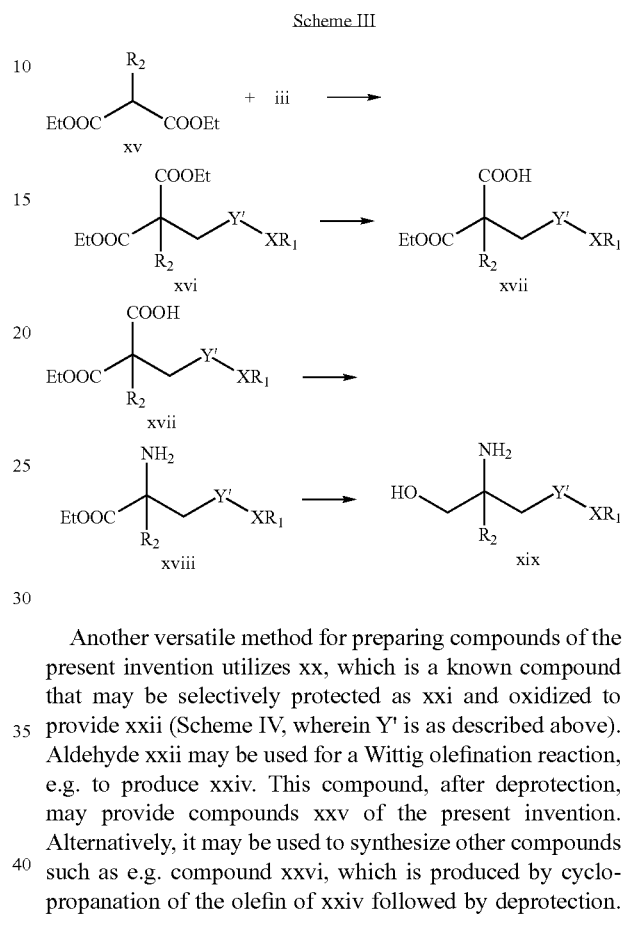

Another versatile method for preparing compounds of the present invention utilizes xx, which is a known compound that may be selectively protected as xxi and oxidized to provide xxii (Scheme IV, wherein Y' is as described above). Aldehyde xxii may be used for a Wittig olefination reaction, e.g. to produce xxiv. This compound, after deprotection, may provide compounds xxv of the present invention. Alternatively, it may be used to synthesize other compounds such as e.g. compound xxvi, which is produced by cyclopropanation of the olefin of xxiv followed by deprotection.

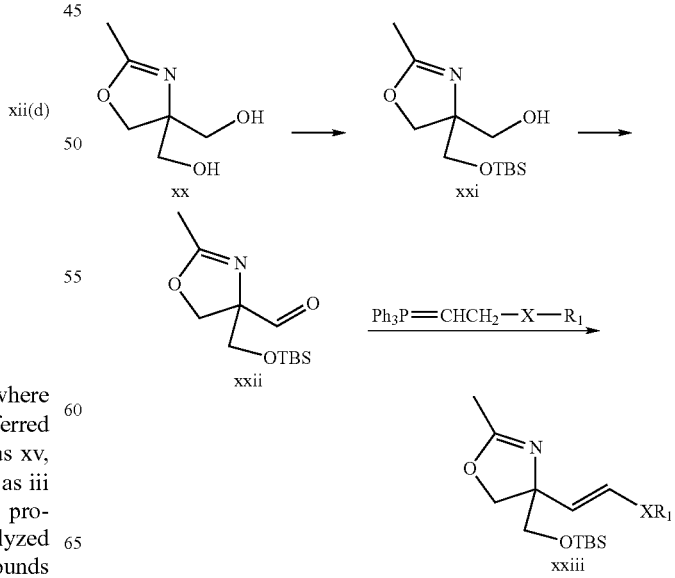

Another general method for preparing compounds where $R_2$ is other than $CH_2OH$ or a residue of formula (h) (referred to herein as $R''_2$), begins with a malonate ester such as xv, which may be alkylated with an alkylating agent such as iii (Scheme III, wherein Y' is as described above). This provides intermediate xvi, which may be selectively hydrolyzed under conditions known in the art to give xvii. Compounds of this general structure may be converted to an amide or -continued

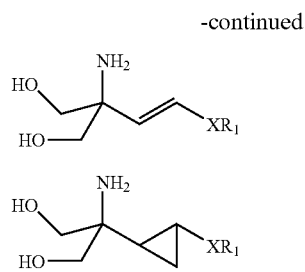

Certain compounds from the above schemes serve as versatile intermediates that allow further functionalization of the X group (Scheme V, wherein Y' is as described above). For example, compounds such as iv, x, xvi, and xxiii have their hydroxy and amine groups protected; when X in such compounds is X' containing certain functional groups, they may be used to introduce new features on X. For example, if X' is a bromophenyl, bromopyridyl or similar group suitable for Suzuki reactions and similar palladium-catalyzed coupling reactions, X' may be arylated to provide biaryl compounds of the present invention, e.g. compounds of Formula I containing a biaryl group, like xxvi.

Alternatively, such bromophenyl and similar compounds may be carboxylated in the presence of a palladium catalyst and $CO_2$, and the carboxyl group may be used to introduce features such as an amide group. Furthermore, such bromophenyl and similar compounds may be carbonylated in the presence of palladium catalyst and CO, to introduce an aldehyde group. The aldehyde may then be used e.g. in Grignard or Wittig reactions to introduce new alkyl or aryl groups, or it may e.g. be converted into an oxime by reaction with hydroxylamine. Oximes such as xxix may be used to generate nitrile oxide intermediates by procedures well known in the art, and these readily undergo [3+2] cycloaddition reactions with olefins and acetylenes to produce isoxazolines and isoxazoles, respectively.

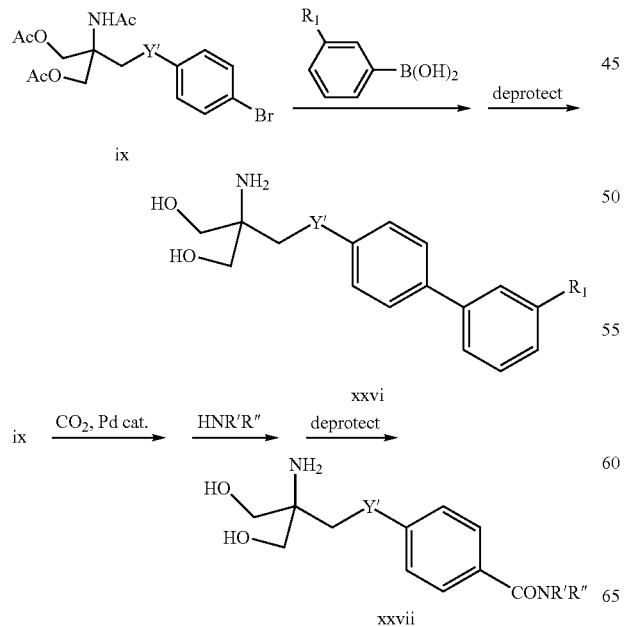

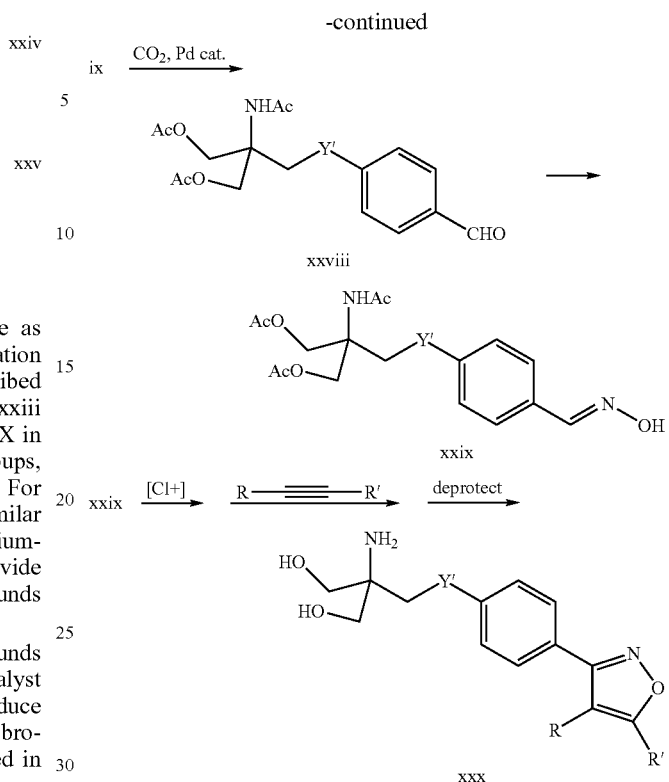

Furthermore, using protected intermediates such as xxiii above, an aryl ring X may be converted readily by methods known in the art to an arylboronic acid or an aryltrimethyltin species that may be used in Suzuki or Stille type coupling reactions to produce other biaryl compounds of the present invention.

Alternatively, a starting compound wherein X contains a nitro group as a substituent, that group may be reduced and alkylated, acylated or sulfonylated to produce other compounds of the present invention. A hydroxy group present in protected form may be deprotected and alkylated or otherwise modified, including being converted into a trifluoromethylsulfonate ("triflate") or similar functional group that is useful for palladium-catalyzed replacement reactions. Other substituents may likewise be incorporated on the aryl groups of intermediates such as those illustrated, as those of skill in the art will appreciate, and may also be transformed using well known methods into other groups to provide other compounds of the present invention. Examples of some very versatile intermediates of this type are shown below:

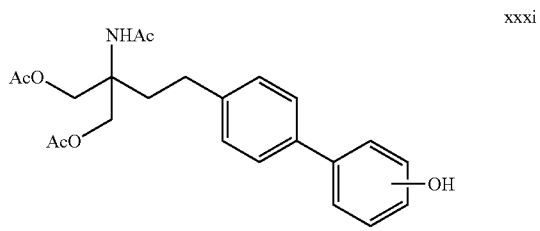

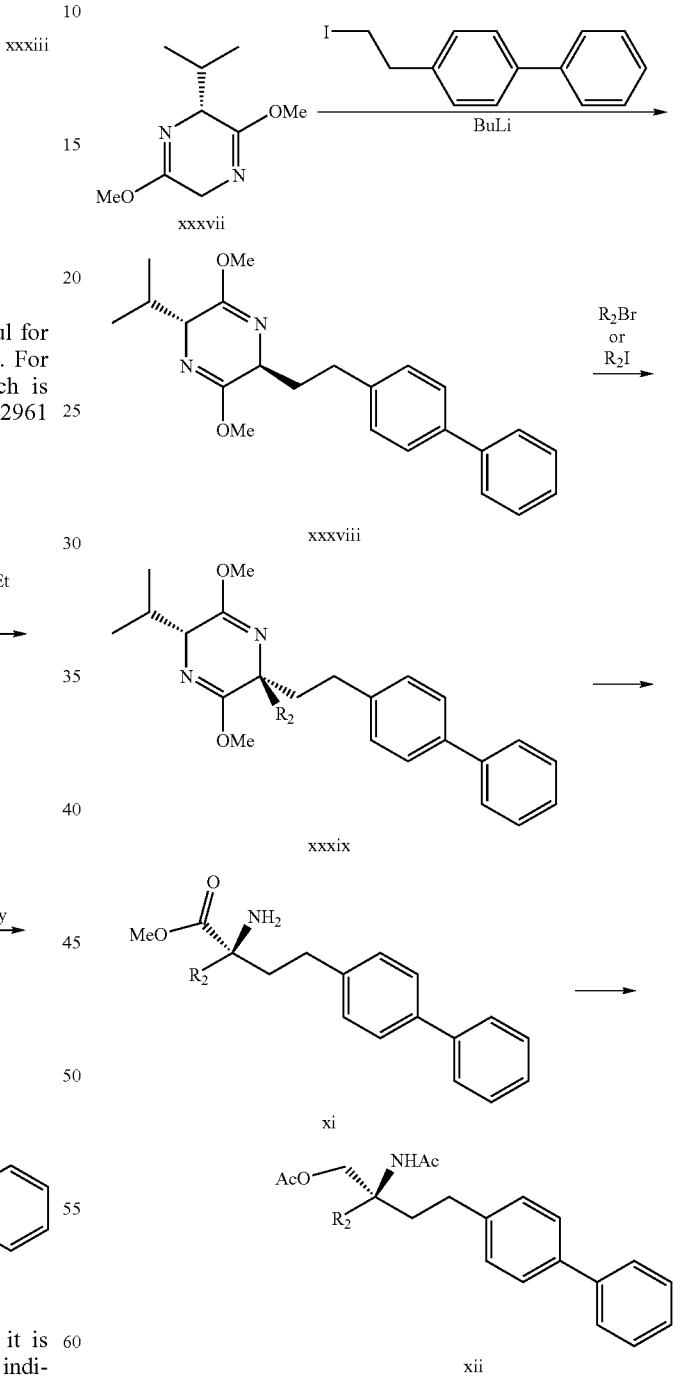

Certain key intermediates that are particularly useful for practicing the present invention are known in the art. For example, compound xxxvi, the preparation of which is described by Kiuche et al. in *J. Med. Chem.*, 43:2946–2961 (2000).

For some embodiments of the present invention, it is desirable to prepare compounds wherein $R_2$ is $R''_2$ as individual enantiomers. These may be obtained by methods described herein, and the individual enantiomers may be separated by methods such as crystallization or chiral chromatography as is known in the art. However, it is also possible to synthesize the individual enantiomers by chiral synthetic methods, using Schöllkopt methodology, for example. Both enantiomers may be prepared using this synthetic route and proper selection of the chiral auxiliary group. By sequential alkylation of the chiral template xxxvii, compound xxxviii is produced diastereoselectively. The chiral intermediate xli may be obtained therefrom by subsequent transformations including hydrolysis, reduction and protection.

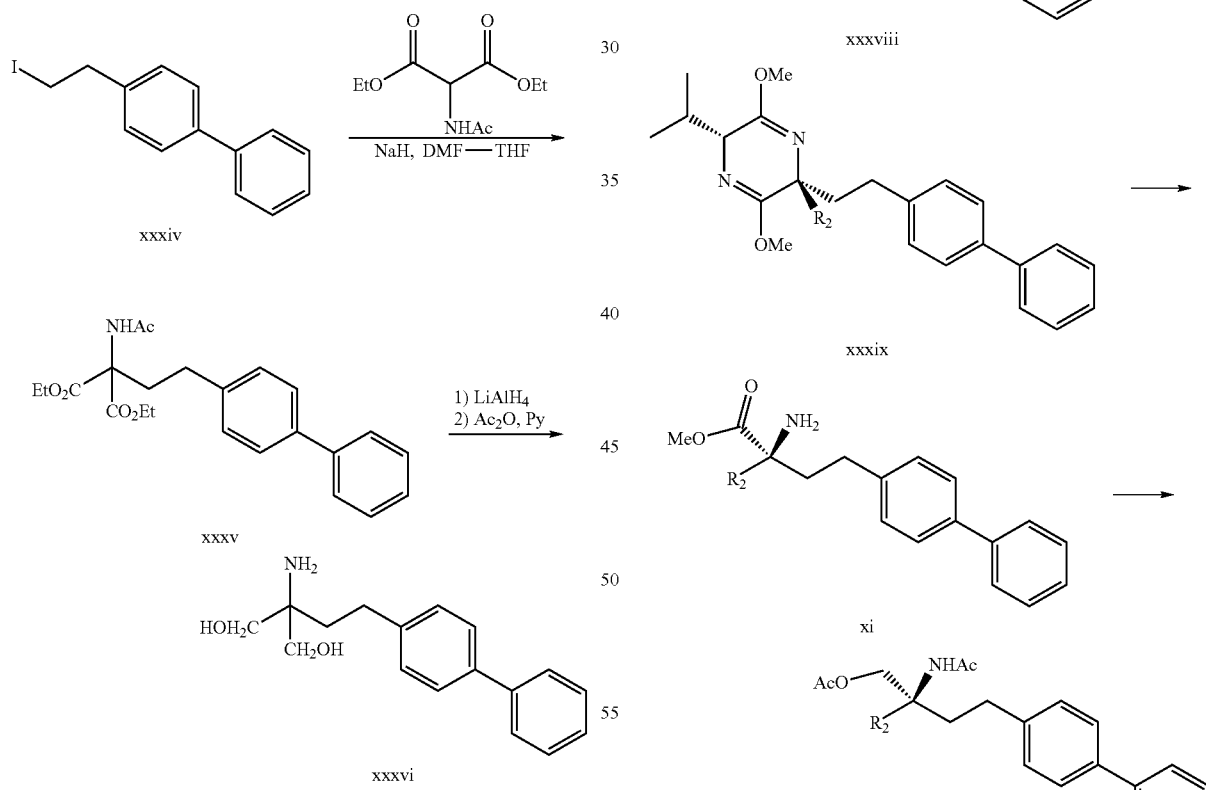

Insofar as the production of the starting materials is not particularly described, the compounds are known or may be prepared analogously to methods known in the art or as disclosed in the Examples hereinafter.

The following Examples are illustrative of the invention.

| | |
|---|---|
| RT = | room temperature |
| DCM = | dichloromethane |
| Bn = | benzyl |

EXAMPLE 1

(R)-2-Amino-4-(4'-butyl-biphenyl-4-yl)-2-methyl-butan-1-ol

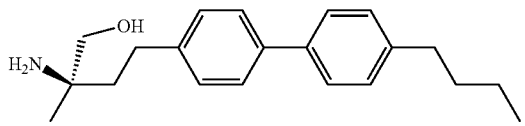

a) (R)-4-(4-Benzyloxy-phenyl)-2-tert-butoxycarbo-nylamino-2-methyl-butyric acid ethyl ester

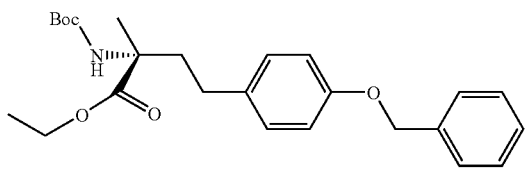

To a solution of (2R,5R)-2-[2-(4-benzyloxy-phenyl)-ethyl]-3,6-diethoxy-5-isopropyl-2-methyl-2,5-dihydro-pyrazine (6.9 g, prepared as disclosed in WO 02/76695 the contents of which being herein incorporated by reference) in dry dioxane (170 ml) is added 105 ml of 0.5N HCl in water. After the homogenous solution is left standing overnight, ethyl acetate (300 ml) is added and the mixture is extracted with water (3×150 ml). The organic phase is dried (MgSO$_4$) and the solvent is evaporated. The crude product is dissolved in DCM and after addition of t-butyloxycarbonylanhydride (5.17 g) is left standing overnight. The solvent is removed in vacuo and the crude residue is purified by chromatography using diethyl ether/hexane (1/5) (R$_f$=0.2, MS: (ES+): 428.5 (M+H)$^+$).

b) (R)-2-tert-Butoxycarbonylamino-2-methyl-4-(4-trifluoromethanesulfonyloxy-phenyl)-butyric acid ethyl ester

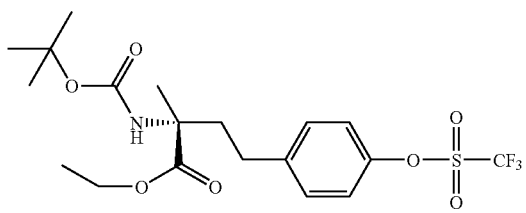

(R)-4-(4-Benzyloxy-phenyl)-2-tert-butoxycarbony-lamino-2-methyl-butyric acid ethyl ester (2.78 g) is dissolved in ethyl acetate (100 ml) and hydrogenated at atmospheric pressure and RT using Pd/C (500 mg) for 16 h. Filtration over talcum is followed by removal of the solvent in vacuo to yield a colorless oil (R$_f$(diethyl ether/hexane=1/1)=0.32, MS: (ES+): 338.4 (M+H)$^+$). The crude phenol (2.20 g) and pyridine (2.6 ml) are dissolved in DCM and cooled to 0° C. Trifluoromethane sulfonic anhydride (1.3 ml) is added dropwise and the mixture is stirred at 0° C. for 30 min. After addition of water (20 ml) and DCM (30 ml), the mixture is washed with 0.5N NaOH (15 ml), water (20 ml), 1 M citric acid (2×25 ml) and water (20 ml). The organic phase is dried over MgSO$_4$, the solvent removed and the crude material purified by chromatography using diethyl ether/hexane (1/2) giving the desired product as colorless oil (R$_f$=0.44, MS: (ES+): 470.5 (M+H)$^+$).

c) (R)-2-tert-Butoxycarbonylamino-4-(4'-butyl-biphenyl-4-yl)-2-methyl-butyric acid ethyl ester

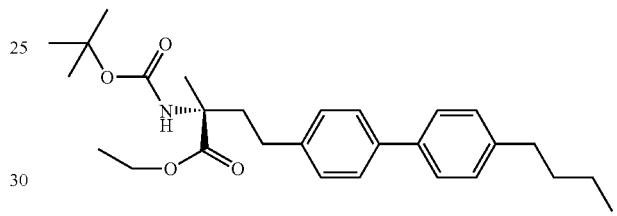

(R)-2-tert-Butoxycarbonylamino-2-methyl-4-(4-trifluoromethane sulfonyloxy-phenyl)-butyric acid ethyl ester (100 mg), 4-butylboronic acid (75 mg) and K$_2$CO$_3$ (44 mg) are suspended in dry toluene (3 ml). Argon is bubbled through the mixture for 10 min., tetrakispalladiumtriphenyl-phosphine (5 mg) is added and the mixture is stirred at 95° C. under Argon for 16 h. After cooling to RT, ethyl acetate (5 ml) is added and the mixture is washed with 0.5N NaOH (2 ml), water (2 ml), 1M citric acid (2×2 ml) and water (2 ml). The organic phase is dried over MgSO$_4$, the solvent removed and the crude material purified by chromatography using diethylether/hexane=1/5 (R$_f$=0.14, MS: (ES+): 454.6 (M+H)$^+$).

d) (R)-2-Amino-4-(4'-butyl-biphenyl-4-yl)-2-methyl-butan-1-ol

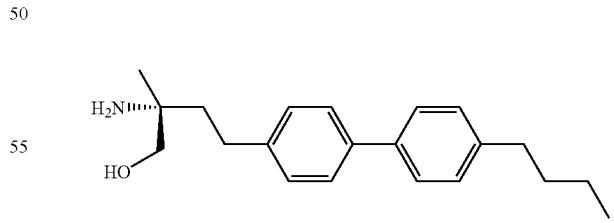

To a solution of (R)-2-tert-butoxycarbonylamino-4-(4'-butyl-biphenyl-4-yl)-2-methyl-butyric acid ethyl ester (22 mg) in diethylether is added lithium borohydride (20 mg). After stirring the suspension for 9 h at RT, ethyl acetate (5 ml) is added and the mixture is washed with water (2 ml), 1M citric acid (2×2 ml) and water (2 ml). The organic phase is dried over MgSO$_4$, the solvent removed and the crude material purified by chromatography using diethyl ether/ hexane (1/1) (R$_f$=0.31, MS: (ES+): 412.6 (M+H)$^+$). The purified product is dissolved in dioxane containing 4M HCl and left at room temperature for 16 h. After lyophilisation, the desired compound is obtained as a white solid in the hydrochloride salt form (R$_f$=0.48 in DCM/methanol 100/15, MS: (ES+): 312.5 (M+H)$^+$).

EXAMPLE 2

(R)-2-Amino-4-(4'-vinyl-biphenyl-4-yl)-2-methyl-butan-1-ol

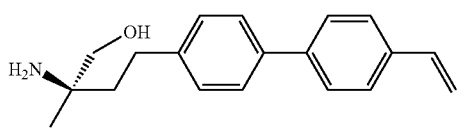

The title compound is obtained by following the procedure as disclosed in Example 1, but using the appropriate starting materials, e.g. vinylphenylboronic acid instead of 4-butylboronic acid in step c). The compound is obtained as an off-white solid, in the hydrochloride salt form. MS: (ES+): 282.4 (M+H)$^+$

EXAMPLE 3

Phosphoric Acid Mono-{(R)-2-amino-4-(4'-butyl-biphenyl-4-yl)-2-methyl butyl} ester

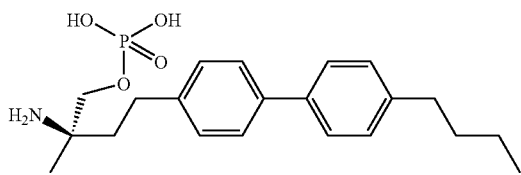

The compound of Example 1c) is converted into the corresponding phosphoric acid monoester by following a procedure as disclosed in WO 02/18395.

EXAMPLE 4

Phosphoric Acid Mono-{(R)-2-amino-4-(4'-vinyl-biphenyl-4-yl)-2-methyl-butyl} ester

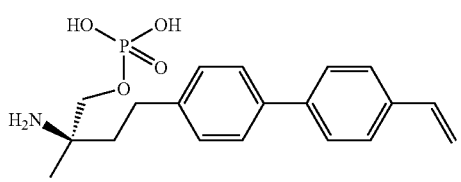

(R)-2-tert-Butoxycarbonylamino-4-(4'-vinyl-biphenyl-4-yl)-2-methyl-butyric acid ethyl ester is converted into the corresponding phosphoric acid monoester by following a procedure as disclosed in WO 02/18395.

EXAMPLE 5

1-[4'-(3-Amino-4-hydroxy-3-hydroxymethyl-butyl)-biphenyl-4yl]-ethanone-O-allyl-oxime

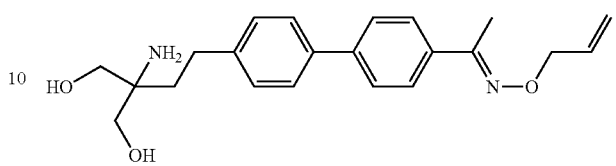

Step A: 2-Acetylamino-2-(2-biphenyl-4-yl-2-oxo-ethyl)-malonic acid diethyl ester Sodium hydride (15 mmol) is added to anhydrous ethanol (50 mL). To this resulting sodium ethoxide solution is added 2-acetylaminomalonic acid diethyl ester (15 mmol) in one portion. The resulting mixture is stirred at room temperature for 30 min. A solution of 4'-phenyl-2-bromoacetophenone (10 mmol) in ethanol (10 mL) is then added and the resulting mixture is stirred at room temperature for 12 h. After concentrating under reduced pressure, the residue is dissolved in EtOAc and water. The organic phase is washed with brine and dried over Na$_2$SO$_4$. After removal of the solvent, the crude material is purified by column chromatography using EtOAc/hexane (1/3) giving the desired product as white solid. $^1$H NMR (400 MHz, CDCl$_3$) δ 8.03 (d, J=8.6 Hz, 2H), 7.68 (d, J=8.6 Hz, 2H), 7.61 (d, J=8.5 Hz, 2H), 7.45 (m, 3H), 7.13 (s, 1H), 4.28 (m, 6H), 1.98 (s, 2H), 1.26 (t, J=7.1 Hz, 6H); MS: (ES$^+$): 412.2 (M+1)$^+$.

Step B: Acetic Acid 4-acetoxy-2-acetoxymethyl-2-acetylamino-4-biphenyl-4-yl-butyl ester To a solution of 2-acetylamino-2-(2-biphenyl-4-yl-2-oxo-ethyl)-malonic acid diethyl ester (5 mmol) in 95% EtOH (50 mL) is added NaBH$_4$ (25 mmol) in portions. After stirring at room temperature for 3 h, the reaction is quenched with saturated NH$_4$Cl. After removal of EtOH under reduced pressure, the aqueous solution is extracted with EtOAc. The organic phase is washed with brine and dried over Na$_2$SO$_4$. After concentrating, the residue is dissolved in anhydrous CH$_2$Cl$_2$ (25 mL). Ac$_2$O (30 mmol) and pyridine (60 mmol) are then added. After stirring at room temperature for 12 h, it is sequentially washed with 1 N HCl, saturated NaHCO$_3$, and brine and dried over Na$_2$SO$_4$. After removal of the solvent, the crude material is purified by column chromatography using EtOAc/hexane (1/1) to give desired product as a white solid. MS: (ES$^+$): 456.2 (M+1)$^+$.

Step C: Acetic Acid 2-acetoxymethyl-2-acetylamino-4-biphenyl-4-yl-butyl Ester

Acetic acid 4-acetoxy-2-acetoxymethyl-2-acetylamino-4-biphenyl-4-yl-butyl ester (5 mmol) is dissolved in EtOH (50 mL) and hydrogenated at atmospheric pressure using 10% Pd-C (10%) at room temperature for 12 h. After filtration and concentration, the crude product is obtained as a white solid and used in the next step without further purification. MS: (ES$^+$): 398.2 (M+1)$^+$.

Step D: Acetic Acid 2-acetoxymethyl-2-acetylamino-4-(4'-acetylbiphenyl-4-yl)-butyl ester To a suspension of AlCl$_3$ (16 mmol) in DCE (20 mL) is added AcCl (8 mmol) in one portion. After stirring at room temperature for 30 min, to the solution is added acetic acid 2-acetoxymethyl-2-acetylamino-4-biphenyl-4-yl-butyl ester (2 mmol) in DCE (5 mL). After an additional 30 min, the mixture is poured into ice-cold 1 N NaOH and is extracted with DCM. The organic phase is washed with 1 N HCl, brine and dried over $Na_2SO_4$. After concentrating, the crude material is purified by column chromatography using EtOAc/hexane (2/1) to give the desired product as a white solid. MS: ($ES^+$): 439.2 $(M+1)^+$.

Step E: 1-[4'-(3-Amino-4-hydroxy-3-hydroxymethyl-butyl)-biphenyl-4-yl]ethanone-O-allyl-oxime To a solution of 1-[4'-(3-amino-4-hydroxy-3-hydroxymethyl-butyl)-biphenyl-4-yl]ethanone-O-allyl-oxime (0.2 mmol) in MeOH (1 mL) is added O-allylalkoxylamine hydrochloride salt (0.24 mmol) and $Et_3N$ (0.23 mmol). After stirring at room temperature for 12 h, it is concentrated and the residue is dissolved in DCM, which is washed with brine and dried over $Na_2SO_4$. After the concentration, the crude product is dissolved in THF (1 mL) and treated with 2 N LiOH aqueous solution (0.5 mL). The resulting mixture is stirred at reflux for 1 h and diluted with $H_2O$ (10 mL). It is then extracted with EtOAc (3×5 mL) and the combined organic phase is washed with brine and dried over $Na_2SO_4$. After concentrating, the crude product is purified with LC-MS to give the desired product as a white solid. $^1$H NMR (400 MHz, $CDCl_3$) δ 8.03 (d, J=8.6 Hz, 2H), 7.68 (d, J=8.6 Hz, 2H), 7.61 (d, J=8.5 Hz, 2H), 7.45 (m, 3H), 7.13 (s, 1H), 4.28 (m, 6H), 1.98 (s, 2H), 1.26 (t, J=7.1 Hz, 6H); MS: ($ES^+$): 369.2 $(M+1)^+$.

By repeating the procedure described in Example 5, using appropriate starting materials, the following compounds of Formula I are obtained as identified in Table I.

TABLE I

| Example No. | A | $R_6$ | $R_7$ | Physical Data MS (M + 1) |
|---|---|---|---|---|
| 6 | H | —$(CH_2)_2CH_3$ | —$CH_3$ | 371.2 |
| 7 | H | —$CH_3$ | —H | 329.2 |
| 8 | H | —$CH_3$ | —$CH_3$ | 343.2 |
| 9 | H | —$CH_2CH_3$ | —$CH_3$ | 357.2 |
| 10 | H | —$(CH_2)_3CH_3$ | —$CH_3$ | 385.2 |
| 11 | H | —$(CH_2)_2CH_3$ | —$CH_2CH_3$ | 385.2 |
| 12 | H | —$(CH_2)_2CH_3$ | —$CH_2CH=CH_2$ | 397.2 |
| 13 | H | —$CH_2CH_3$ | —H | 343.2 |
| 14 | H | —$CH_2CH_3$ | —$CH_2CH_3$ | 371.2 |
| 15 | H | —$CH_2CH_3$ | —$CH_2CH=CH_2$ | 383.2 |
| 16 | H | —CH(cyclopropyl) | —$CH_2CH=CH_2$ | 395.3 |
| 17 | H | —$(CH_2)_3CH_3$ | —$CH_2CH=CH_2$ | 411.3 |
| 18 | H | —$(CH_2)_3CH_3$ | —$CH_2CH_3$ | 399.3 |
| 19 | H | —$(CH_2)_4CH_3$ | —$CH_2CH=CH_2$ | 425.3 |
| 20 | H | —$(CH_2)_4CH_3$ | —$CH_2CH_3$ | 413.3 |
| 21 | H | —$(CH_2)_6CH_3$ | —$CH_2CH=CH_2$ | 453.3 |
| 22 | —$CH_3$ (meta) | —$CH_3$ | —$CH_2CH=CH_2$ | 383.2 |
| 23 | H | H | —$CH_2CH=CH_2$ | 355.2 |
| 24 | H | —$CH_3$ | —$(CH_2)_3CH_3$ | 385.2 |
| 25 | H | —$CH_3$ | —$(CH_2)_2CH_3$ | 371.2 |
| 26 | H | —$CH_3$ | —$(CH_2)_4CH_3$ | 399.2 |
| 27 | H | —$CH_3$ | —$(CH_2)_5CH_3$ | 413.2 |
| 28 | I (meta) | —$CH_3$ | —$(CH_2)_2CH_3$ | |
| 28.1 | F (meta) | —$CH_3$ | —$(CH_2)_2CH_3$ | 389.2 |
| 29 | I (meta) | —$CH_3$ | —$CH_2CH=CH_2$ | |
| 29.1 | F (meta) | —$CH_3$ | —$CH_2CH=CH_2$ | 387.2 |
| 30 | I (ortho) | —$CH_3$ | —$CH_2CH=CH_2$ | |
| 30.1 | F (ortho) | —$CH_3$ | —$CH_2CH=CH_2$ | 387.2 |
| 31 | I (ortho) | —$CH_3$ | —$(CH_2)_2CH_3$ | |
| 31.1 | F (ortho) | —$CH_3$ | —$(CH_2)_2CH_3$ | 389.2 |
| 32 | H | —$CH_3$ | —$CH_2C\equiv CH$ | 367.2 |

TABLE I-continued

| | | | | Physical Data |
|---|---|---|---|---|
| Example No. | A | $R_6$ | $R_7$ | MS (M + 1) |
| 33 | | | | 369.2 |
| 34 | | | | 369.2 |

EXAMPLE 35

2-Amino-2-[2-(4'-hexylbiphenyl-4-yl)-ethyl]propane-1,3-diol

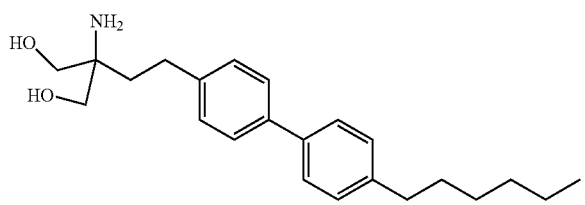

Step A: Acetic Acid 2-acetoxymethyl-2-acetylamino-4-(4'-hexyl-biphenyl-4-yl)-butyl ester To a solution of acetic acid 2-acetoxymethyl-2-acetylamino-4-(4'-hexanoyl-biphenyl-4-yl)-butyl ester (prepared according to Scheme 1) (1 mmol) in trifluoroacetic acid (10 mL) is added triethylsilane (2.5 mmol). The resulting mixture is stirred at room temperature for 12 h. After concentrating under reduced pressure, the residue is dissolved in DCM and the organic solution is washed with saturated NaHCO$_3$ and brine and dried over Na$_2$SO$_4$. After concentration, the crude product is purified by column chromatography using EtOAc/hexane (1/1) to give the desired compound as a white solid. MS: (ES$^+$): 482.3 (M+1)$^+$.

Step B: 2-Amino-2-[2-(4'-hexylbiphenyl-4-yl)-ethyl]propane-1,3-diol

Acetic acid 2-acetoxymethyl-2-acetylamino-4-(4'-hexyl-biphenyl-4-yl)-butyl ester (0.2 mmol) is dissolved in THF (1 mL) and treated with 2 N LiOH aqueous solution (0.5 mL). The resulting mixture is stirred at reflux for 1 h and diluted with H$_2$O (10 mL). It is then extracted with EtOAc (3×5 mL) and the combined organic phase is washed with brine and dried over Na$_2$SO$_4$. After concentrating, the crude product is purified with LC-MS to give the desired product as a white solid. MS: (ES$^+$): 356.2 (M+1)$^+$.

By repeating the procedure described in Example 35, using appropriate starting materials, the following compounds of Formula I are obtained as identified in Table II.

TABLE II

[Structure: biphenyl with -CH2CH2-C(NH2)(CH2OH)2 on one ring and R on the other]

| Example No. | R | Physical Data MS (M + 1) |
|---|---|---|
| 36 | —(CH₂)₄CH₃ | 342.2 |
| 37 | —(CH₂)₇CH₃ | 384.3 |
| 38 | —C(=CHCH₂CH₃)(CH₂)₂CH₃ | 368.3 |
| 39 | [Structure: HOCH2-C(NH2)(CH3)-CH2CH2-biphenyl-(CH2)4CH3] | 326.2 |

EXAMPLE 40

2-Amino-2-{2-[4'-(5-propyl-isoxazol-3-yl)-biphenyl-4-yl]-ethyl}-propane-1,3-diol

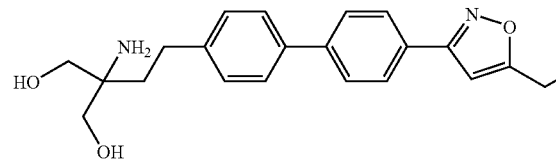

Step A: 4-[2-(4-Bromophenyl)vinyl]-4-(t-butyldimethylsilanyloxymethyl)-2-methyl-4,5-dihydrooxazole To a suspension of (4-bromobenzyl)triphenyl-phosphonium bromide (6 mmol) in dry THF (25 mL) is added NaH (6 mmol) in portions. After stirring at room temperature for 30 min, a solution of 4-(t-butyidimethylsilanyloxymethyl)-2-methyl-4,5-dihydrooxazole-4-carbaldehyde (prepared according to Scheme 3 using well-known chemistry in the art) (5 mmol) in THF (10 mL) is added in one portion. The mixture is stirred at room temperature for 12 h. After concentration, the residue is treated with EtOAc/hexane (1/5) (100 mL) and the solid is filtered. The filtrate is washed with brine and dried over Na₂SO₄. After concentration, the crude product is purified by column chromatography by EtOAc/hexane (1/5) to give the desired product as a colorless oil. MS: (ES⁺): 410.1 (M+1)⁺.

Step B: 4-[2-(4-Bromophenyl)ethyl]-4-(t-butyldimethylsilanyloxymethyl)-2-methyl-4,5-dihydrooxazole 4-[2-(4-Bromophenyl)vinyl]-4-(t-butyldimethylsilanyloxymethyl)-2-methyl-4,5-dihydrooxazole (3 mmol) is dissolved in ethanol (15 mL) and hydrogenated at atmospheric pressure in the presence of chlorotris(triphenylphosphine)rhodium(I) (10%). The mixture is stirred at 40° C. for 12 h. After filtration and concentration, the crude product is obtained as colorless oil, which is used directly in the next step without further purification. MS: (ES⁺): 412.1 (M+1)⁺.

Step C: 4-{2-[4-(t-butyldimethylsilanyloxymethyl)-2-methyl-4,5-dihydrooxazol-4-yl]ethyl}-biphenyl-4-carbaldehyde The mixture of 4-[2-(4-bromophenyl)ethyl]-4-(t-butyldimethylsilanyloxymethyl)-2-methyl-4,5-dihydrooxazole (2 mmol), 4-fomylphenylboronic acid (2.4 mmol), Pd(PPh₃)₄ (0.2 mmol) and Na₂CO₃ (9.6 mmol) in toluene (5 mL), EtOH (1.5 mL) and H₂O (5 mL) is stirred at 90° C. for 5 h. It is diluted with H₂O (15 mL) and EtOAc (15 mL) and the organic phase is washed with brine and dried over Na₂SO₄. After concentration, the crude product is purified by column chromatography using EtOAc/hexane (1/4) to give the desired product as a white solid. MS: (ES⁺): 438.2 (M+1)⁺.

Step D: Acetic Acid 2-acetoxymethyl-2-acetylamino-4-(4'-formylbiphenyl-4-yl)butyl ester To a solution of 4-{2-[4-(t-Butyidimethylsilanyloxymethyl)-2-methyl-4,5-dihydrooxazol-4-yl]ethyl}-biphenyl-4-carbaldehyde (2 mmol) in THF (10 mL) is added 1 N HCl aqueous solution (5 mL). The mixture is refluxed for 2 hours. After cooling to room temperature, it is neutralized by saturated Na₂CO₃ and extracted with EtOAc (20×3). The combined organic phase is washed with brine and dried over Na₂SO₄. After concentrating, the residue is dissolved in dry DCM (10 mL) and is treated with Ac₂O (8 mmol) and pyridine (16 mmol). After stirring at room temperature for 12 h, the solution is washed with 1 N HCl and brine and dried over Na₂SO₄. After concentrating, the crude product is purified by column chromatography using EtOAc/hexane (1/1) to give the desired product as white solid. MS: (ES⁺): 426.2 (M+1)⁺.

Step E: Acetic Acid 2-acetoxymethyl-2-acetylamino-4-[4'-(hydroxyiminomethyl)-biphenyl-4-yl] butyl ester To a solution of acetic acid 2-acetoxymethyl-2-acetylamino-4-(4'-formyl-biphenyl-4-yl) butyl ester (1 mmol) in methanol (10 mL) is added $NH_2OH \cdot HCl$ (1.2 mmol) and $Et_3N$ (1.1 mmol). The mixture is stirred at room temperature 12 hours. After concentrating, the residue is dissolved in DCM (20 mL) and washed with $H_2O$ and brine. The crude product, after concentration, is used in the next step without further purification. MS: $(ES^+)$: 441.2 $(M+1)^+$.

Step F: Acetic Acid 2-acetoxymethyl-2-acetylamino-4-[4'-(5-propyl-isoxazol-3-yl)biphenyl-4-yl] butyl ester A mixture of acetic acid 2-acetoxymethyl-2-acetylamino-4-[4'-(hydroxyimino-methyl)biphenyl-4-yl]butyl ester (0.2 mmol), NaOCl (2 mmol), $Et_3N$ (3 mmol) and pentyne (40 mmol) in DCM (4 mL) and $H_2O$ (1 mL) is stirred at room temperature for 12 h. It is diluted with DCM (5 mL) and $H_2O$ (10 mL) and the organic phase is washed with brine and dried over $Na_2SO_4$. After concentrating, the crude product is purified by column chromatography using EtOAc/hexane (1/1) to give the desired product as a white solid. MS: $(ES^+)$: 507.2 $(M+1)^+$.

Step G: 2-Amino-2-{2-[4'-(5-propyl-isoxazol-3-yl)-biphenyl-4-yl]ethyl}propane-1,3-diol Acetic acid 2-acetoxymethyl-2-acetylamino-4-[4'-(5-propyl-isoxazol-3-yl)-biphenyl-4-yl]butyl ester (0.1 mmol) is dissolved in THF (1 mL) and treated with 2 N LiOH aqueous solution (0.5 mL). The resulting mixture is stirred at reflux for 1 h and diluted with $H_2O$ (10 mL). It is then extracted with EtOAc (3×5 mL) and the combined organic phase is washed with brine and dried over $Na_2SO_4$. After concentrated, the crude product is purified with LC-MS to give the desired product as a white solid. $^1$H NMR (400 MHz, $CD_3OD$) δ 7.86 (d, J=8.4 Hz, 2H), 7.70 (d, J=8.4 Hz, 2H), 7.58 (d, J=8.2 Hz, 2H), 7.33 (d, J=8.2 Hz, 2H), 3.53 (q, J=11.0 Hz, 4H), 2.81 (t, J=7.4 Hz, 2H), 2.71 (m, 2H), 1.79 (m, 4H), 1.04 (t, J=7.4 Hz, 3H). MS: $(ES^+)$: 381.2 $(M+1)^+$.

By repeating the procedure described in Example 40, using appropriate starting materials, the following compounds of formula I are obtained as identified in Table III.

TABLE III

| Example No. | Structure | Physical Data MS (M + 1) |
|---|---|---|
| 41 | (structure: 2-amino-2-{2-[4'-(5-propyl-isoxazol-3-yl)biphenyl-4-yl]ethyl}propane-1,3-diol) | 381.2 |
| 42 | (structure: 2-amino-2-{2-[4'-(5-propyl-4,5-dihydro-isoxazol-3-yl)biphenyl-4-yl]ethyl}propane-1,3-diol) | 383.2 |

By repeating the appropriate procedure described above, using materials, the following compounds of formula I are obtained as IV, V and VI.

TABLE IV

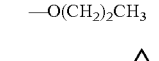

| Example No. | R¹ | Physical Data MS (M + 1) |
|---|---|---|
| 43 | (3-methyl-isoxazol-5-yl)-pentyl | 333.2 |
| 44 | (2-methyl-benzoxazol-5-yl)-tert-butyl | 369.2 |
| 45 | (5-methyl-thiophen-2-yl)-heptyl | 376.2 |
| 46 | (5-methyl-thiophen-2-yl)-pentyl | 348.2 |
| 47 | (5-methyl-thiophen-2-yl)-ethyl-(4-butoxy-phenyl) | 454.2 |

TABLE V

| Example No. | R | Physical Data MS (M + 1) |
|---|---|---|
| 48 | —O(CH₂)₂CH₃ | 330.2 |
| 49 | —OCH₂-cyclopropyl | 342.2 |
| 50 | —O(CH₂)₃CH₃ | 344.2 |
| 51 | —OCH₂CH₃ | 316.2 |
| 52 | —O(CH₂)₂CH(CH₃)₂ | 358.2 |
| 53 | —O(C₆H₅) | 364.2 |
| 54 | —O(CH₂)₄CH₃ | 358.2 |

TABLE V-continued

[Structure: biphenyl with 2-amino-2-(hydroxymethyl)-propanediol group and R substituent on the distal phenyl]

| Example No. | R | Physical Data MS (M + 1) |
|---|---|---|
| 55 | [3-(methoxymethyl)-5-methylisoxazole] | 383.2 |
| 56 | —O(CH$_2$)$_2$(C$_6$H$_5$) | 392.2 |
| 57 | [cyclopentyloxymethyl] | 356.2 |
| 58 | —O(CH$_2$)$_2$OCH$_2$CH$_3$ | 360.2 |
| 59 | —O(CH$_2$)$_2$OCH$_3$ | 346.2 |
| 60 | —O—CH$_2$—(4-fluorophenyl) | 396.2 |
| 61 | —O—CH$_2$—(3,5-difluorophenyl) | 414.2 |
| 62 | —O—CH$_2$—(4-trifluoromethylphenyl) | 446.2 |
| 63 | —O—CH$_2$—(3,4-difluorophenyl) | 414.2 |
| 64 | —(CH$_2$)$_2$—(4-cyanophenyl) | 401.2 |

TABLE VI

[Structure: pyridine-phenyl with 2-amino-2-(hydroxymethyl)-propanediol group and R substituent]

| Example No. | R | Physical Data MS (M + 1) |
|---|---|---|
| 65 | H | 272.2 |
| 66 | —C(O)(CH$_2$)$_2$CH$_3$ | 342.2 |

TABLE VI-continued

[Structure: biphenyl with H2N-C(CH2OH)2-CH2CH2- group on one ring and R on the other ring para position]

| Example No. | R | Physical Data MS (M + 1) |
|---|---|---|
| 67 | —CH(OH)(CH$_2$)$_2$CH$_3$ | 344.2 |
| 68 | —C(O)CH$_2$CH$_3$ | 328.2 |
| 69 | —C(O)(CH$_2$)$_3$CH$_3$ | 356.2 |
| 70 | —(CH$_2$)$_3$CH$_3$ | 328.2 |
| 71 | —CH(OH)CH$_2$CH$_3$ | 330.2 |
| 72 | —CH(OH)(CH$_2$)$_3$CH$_3$ | 358.2 |
| 73 | —(CH$_2$)$_2$CH$_3$ | 314.2 |
| 74 | —C(=NOH)(CH$_2$)$_2$CH$_3$ | 357.2 |
| 75 | —C(=NOH)(CH$_2$)$_3$CH$_3$ | 371.2 |
| 76 | —C(=NOCH$_2$CH$_3$)CH$_3$ | 357.2 |
| 77 | [cyclopropyl-C(CH$_3$)=N-O-CH$_3$] | 369.2 |
| 78 | [cyclopropyl-C(CH$_3$)=N-O-CH$_2$CH$_3$] | 383.2 |
| 79 | —C(=NOCH$_2$CH$_3$)(CH$_2$)$_6$CH$_3$ | 441.3 |
| 80 | —CH(CH$_2$CH$_3$)(CH$_2$)$_2$CH$_3$ | 356.3 |
| 81 | —CH((CH$_2$)$_2$CH$_3$)$_2$ | 370.3 |
| 82 | —NHS(O)$_2$CH$_3$ | 365.2 |
| 83 | —NH$_2$ | 287.2 |
| 84 | —C(O)NH(CH$_2$)$_3$CH$_3$ | 371.2 |
| 85 | —CH$_2$CN | 311.2 |
| 86 | —OCH$_2$CN | 327.2 |
| 87 | —OCH$_2$C≡CH | 326.2 |
| 88 | —OH | 288.2 |
| 89 | —O(CH$_2$)$_3$F | 348.2 |
| 90 | —O(CH$_2$)$_7$CH$_3$ | 400.3 |
| 91 | —O(CH$_2$)$_6$CH$_3$ | 386.3 |
| 92 | [biphenyl structure with NH$_2$/HO/OH group and propyl ketone O-methyl oxime] | 371.2 |
| 93 | [biphenyl structure with NH$_2$/HO/OH group and methyl ketone O-propyl oxime] | 371.2 |
| 94 | [phenyl-benzodioxole structure with NH$_2$/HO/OH group] | 316.2 |

The compounds of formula I in free form or in pharmaceutically acceptable salt form, exhibit valuable pharmacological properties, e.g. lymphocyte recirculation modulating or anti-angiogenic properties, e.g. as indicated in in vitro and in vivo tests and are therefore indicated for therapy.

A. In vitro: Binding Affinity of Compounds of Formula I to Individual Human S1P Receptors may be Determined in the Following Assays:

Transient Transfection of Human S1P Receptors into HEK293 Cells

EDG receptors and $G_i$ proteins are cloned, and equal amounts of 4 cDNAs for the EDG receptor, $G_i$-α, $G_i$-β and $G_i$-γ are mixed and used to transfect monolayers of HEK293 cells using the calcium phosphate precipitate method (M. Wigler et al., Cell. 1977;11;223 and D S. Im et al., Mol. Pharmacol. 2000;57;753). Briefly, a DNA mixture containing 25 μg of DNA and 0.25 M CaCl is added to HEPES-buffered 2 mM $Na_2HPO_4$. Subconfluent monolayers of HEK293 cells are poisoned with 25 mM chloroquine, and the DNA precipitate is then applied to the cells. After 4 hours, the monolayers are washed with phosphate-buffered saline and re-fed media (90% 1:1 Dulbecco's modified essential media (DMEM):F-12+10% fetal bovine serum). The cells are harvested 48–72 hours after addition of the DNA by scraping in HME buffer (in mM: 20 HEPES, 5 $MgCl_2$, 1 EDTA, pH 7.4) containing 10% sucrose on ice, and disrupted using a Dounce homogenizer. After centrifugation at 800×g, the supernatant is diluted with HME without sucrose and centrifuged at 100,000×g for 1 hour. The resulting pellet is rehomogenized and centrifuged a second hour at 100,000×g. This crude membrane pellet is resuspended in HME with sucrose, aliquoted, and snap-frozen by immersion in liquid nitrogen. The membranes are stored at 70° C. Protein concentration is determined spectroscopically by the Bradford protein assay.

| Example | $S1P_1$ $EC_{50}$ [nM] | $S1P_2$ $EC_{50}$ [nM] | $S1P_3$ $EC_{50}$ [nM] | $S1P_4$ $EC_{50}$ [nM] | $S1P_5$ $EC_{50}$ [nM] |
|---|---|---|---|---|---|
| 36 | 0.33 | >10000 | >10000 | 1.2 | 1.1 |
| 41 | 0.16 | >10000 | 53.8 | >10000 | 2.1 |
| 63 | 0.07 | >10000 | 1.9 | >10000 | 0.1 |

GTPγS Binding Assay Using S1P Receptor/HEK293 Membrane Preparations

GTPγS binding experiments are performed as described by D S. Im et al., Mol. Pharmacol. 2000; 57:753. Ligand-mediated GTPγS binding to G-proteins is measured in GTP binding buffer (in mM: 50 HEPES, 100 NaCl, 10 $MgCl_2$, pH 7.5) using 25 μg of a membrane preparation from transiently transfected HEK293 cells. Ligand is added to membranes in the presence of 10 μM GDP and 0.1 nM [$^{35}$S]GTPγS (1200 Ci/mmol) and incubated at 30° C. for 30 min. Bound GTPγS is separated from unbound using the Brandel harvester (Gaithersburg, Md.) and counted with a liquid scintillation counter.

In these assays, the compounds of formula I wherein $R_2$ or $R_5$ is a residue of formula (h) have binding affinities to S1P receptors in the sub-microM range.

B. In Vitro: Antitumor Activity

A mouse breast cancer cell line originally isolated from mammary carcinomas is used, e.g. JygMC(A). The cell number is adjusted to $5 \times 10^5$ for plating in fresh medium before the procedure. Cells are incubated with fresh medium containing 2.5 mM of thymidine without FCS for 12 hours and then washed twice with PBS, followed by addition of fresh medium with 10% FCS and additionally incubated for another 12 hours. Thereafter the cells are incubated with fresh medium containing 2.5 mM of thymidine without FCS for 12 hours. To release the cells from the block, the cells are washed twice with PBS and replated in fresh medium with 10% FCS. After synchronization, the cells are incubated with or without various concentrations of a compound of formula I for 3, 6, 9, 12, 18 or 24 hours. The cells are harvested after treatment with 0.2% EDTA, fixed with ice-cold 70% ethanol solution, hydrolyzed with 250 μg/ml of RNaseA (type 1-A: Sigma Chem. Co.) at 37° C. for 30 minutes and stained with propidium iodide at 10 mg/ml for 20 minutes. After the incubation period, the number of cells is determined both by counting cells in a Coulter counter and by the SRB colorimetric assay. Under these conditions compounds of formula I inhibit the proliferation of the tumor cells at concentrations ranging from $10^{-12}$ to $10^{-6}$ M.

C. In Vitro: S1P-Mediated HUVEC Migration Assay

The migration assay is performed using Fluoro-Blok 24-Multiwell Insert Plates coated with fibronectin (8 μm pore size, Falcon #351147) instead of the individual inserts in a 24-well plate. Cells and test compounds are prepared and preincubated as described above, then 100 μl is added to each appropriate well in the Insert Plate. 300 μl of the EBM-2+2% charcoal-stripped media without S1P is added to the bottoms of the wells marked for no stimulation (−), and 300 μl of the media containing S1P (500 nM) is added to the bottoms of the wells marked for stimulation (+). The plate is then incubated for 4 hours at 37° C., 5% $CO_2$.

Calcein AM, 50 μg/vial, (Molecular Probes #C3100) is prepared by first adding 20 μl DMSO to the vial. Then 12.5 ml of HBSS (per plate) is warmed to 37° C. and 150 μl is added to the vial. The contents of the vial are then transferred back to the remaining HBSS to make the final concentration 4 μg/ml Calcein AM.

The Fluoro-Blok plate is removed from the incubator and the top insert plate is separated and "flicked" to remove excess media clinging to the inserts. The insert plate is then transferred to a fresh 24-well plate containing 500 μl/well of the 4 μg/ml Calcein AM. The plate is then incubated for 1.5 hours at 37° C., 5% $CO_2$.

After incubation, the plate is read on a Cytofluor II at an excitation of 485 nm and emission of 530 nm. The Fluoro-Blok coating in the inserts allows only the cells that have migrated to the bottom to be counted. Data are transferred to Excel for calculations, graphs are created using SigmaPlot, and SigmaStat is used for significance tests (t-test).

D. In Vivo: Blood Lymphocyte Depletion

A compound of formula I or the vehicle is administered orally by gavage to rats. Tail blood for hematological monitoring is obtained on day −1 to give the baseline individual values, and at 2, 6, 24, 48 and 72 hours after drug application. In this assay, the compounds of formula I deplete peripheral blood lymphocytes when administered at a dose of 0.03 to 3 mg/kg. For example compounds of Example 2 and 9 deplete peripheral blood lymphocytes by more than 50% 6 hours after administration of a dose of 0.8 mg/kg and 0.2 mg/kg, respectively.

E. In Vivo: Screening Assays for Measurement of Circulating Lymphocytes and Assessment of Heart Effect Measurement of Circulating Lymphocytes: Compounds are dissolved in DMSO and further diluted with deionized water. Mice (C57bl/6 male, 6–10 week-old) are administered 20 μg of compounds (diluted in 200 μl water, 4% DMSO) via intra-peritoneal (IP) injection under short isoflurane anesthesia. 200 μl water, 4% DMSO, and FTY720 (10 μg) are included as negative and positive controls.

Blood is collected from the retro-orbital sinus 18 hours after drug administration under short isoflurane anesthesia. Whole blood samples are subjected to hematology analysis. Peripheral lymphocyte counts are determined using an automated analyzer (Hemavet 3700). Subpopulations of peripheral blood lymphocytes are stained by fluorochrome-conjugated specific antibodies and analyzed using a fluorescent activating cell sorter (Facscalibur). Two mice are used to assess the lymphocyte depletion activity of each compound screened.

Assessment of Heart Effect: The effects of compounds on cardiac function are monitored using the AnonyMOUSE ECG recording system. ECGs are recorded in conscious mice (C57bl/6 male, 6–10 week-old) before and after compound administration. 90 μg of compound further diluted in 200 μl water and 15% DMSO are injected IP. Four mice are used to assess heart rate effect of each compound.

F. In Vivo: Anti-Angiogenic Activity

Porous chambers containing (i) sphingosine-1-phosphate (5 μM/chamber) or (ii) human VEGF (1 μg/chamber) in 0.5 ml of 0.8% w/v agar (containing heparin, 20 U/ml) are implanted subcutaneously in the flank of mice. S1P or VEGF induces the growth of vascularized tissue around the chamber. This response is dose-dependent and can be quantified by measuring the weight and blood content of the tissue. Mice are treated once a day orally or intravenously with a compound of formula I starting 4–6 hours before implantation of the chambers and continuing for 4 days. The animals are sacrificed for measurement of the vascularized tissues 24 hours after the last dose. The weight and blood content of the vascularized tissues around the chamber is determined. Animals treated with a compound of formula I show reduced weight and/or blood content of the vascularized tissues compared to animals treated with vehicle alone. Compounds of Formula I are anti-angiogenic when administered at a dose of about 0.3 to about 3 mg/kg.

The compounds of formula I are, therefore, useful in the treatment and/or prevention of diseases or disorders mediated by lymphocytes interactions e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

Furthermore, the compounds of formula I are useful in cancer chemotherapy, particularly for cancer chemotherapy of solid tumors, e.g. breast cancer, or as an anti-angiogenic agent.

In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in a conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

1.3 A method for inhibiting or controlling deregulated angiogenesis, e.g. sphingosine-1-phosphate (S1P) mediated angiogenesis, in a subject in need thereof, comprising administering to said subject a therapeutically effective amount of a compound of formula I or a pharmaceutically acceptable salt thereof.

1.4 A method for preventing or treating diseases mediated by a neo-angiogenesis process or associated with deregulated angiogenesis in a subject in need thereof, comprising administering to said subject a therapeutically effective amount of a compound of formula I or a pharmaceutically acceptable salt thereof.

2. A compound of formula I, in free form or in a pharmaceutically acceptable salt form for use as a pharmaceutical, e.g. in any of the methods as indicated under 1.1 to 1.4 above.

3. A pharmaceutical composition, e.g. for use in any of the methods as in 1.1 to 1.4 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 to 1.4 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g. a malignant cell antiproliferative agent. For example the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578 or AP23573; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g. monoclonal antibodies to leukocyte receptors, e.g. MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent.

By the term "chemotherapeutic agent" is meant any chemotherapeutic agent and it includes but is not limited to,
  i. an aromatase inhibitor,
  ii. an anti-estrogen, an anti-androgen (especially in the case of prostate cancer) or a gonadorelin agonist,
  iii. a topoisomerase I inhibitor or a topoisomerase II inhibitor,
  iv. a microtubule active agent, an alkylating agent, an antineoplastic antimetabolite or a platin compound,
  v. a compound targeting/decreasing a protein or lipid kinase activity or a protein or lipid phosphatase activity, a further anti-angiogenic compound or a compound which induces cell differentiation processes,
  vi. a bradykinin 1 receptor or an angiotensin II antagonist,
  vii. a cyclooxygenase inhibitor, a bisphosphonate, a histone deacetylase inhibitor, a heparanase inhibitor (prevents heparan sulphate degradation), e.g. PI-88, a biological response modifier, preferably a lymphokine or interferons, e.g. interferon γ, an ubiquitination inhibitor, or an inhibitor which blocks anti-apoptotic pathways,
  viii. an inhibitor of Ras oncogenic isoforms, e.g. H-Ras, K-Ras or N-Ras, or a farnesyl transferase inhibitor, e.g. L-744,832 or DK8G557,
  ix. a telomerase inhibitor, e.g. telomestatin,
  x. a protease inhibitor, a matrix metalloproteinase inhibitor, a methionine aminopeptidase inhibitor, e.g. bengamide or a derivative thereof, or a proteosome inhibitor, e.g. PS-341, and/or
  xi. a mTOR inhibitor.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. A combination of the invention comprising a chemotherapeutic agent which is an aromatase inhibitor is particularly useful for the treatment of hormone receptor positive tumors, e.g. breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide.

The term "gonadorelin agonist" as used herein includes, but is not limited to abarelix, goserelin and goserelin acetate.

The term "topoisomerase I inhibitor" as used herein includes, but is not limited to topotecan, irinotecan, 9-nitro-camptothecin and the macromolecular camptothecin conjugate PNU-166148 (compound A1 in WO99/17804).

The term "topoisomerase II inhibitor" as used herein includes, but is not limited to the anthracyclines such as doxorubicin, daunorubicin, epirubicin, idarubicin and nemorubicin, the anthraquinones mitoxantrone and losoxantrone, and the podophillotoxines etoposide and teniposide.

The term "microtubule active agent" relates to microtubule stabilizing and microtubule destabilizing agents including, but not limited to taxanes, e.g. paclitaxel and docetaxel, vinca alkaloids, e.g., vinblastine, especially vinblastine sulfate, vincristine especially vincristine sulfate, and vinorelbine, discodermolides and epothilones and derivatives thereof, e.g. epothilone B or a derivative thereof.

The term "alkylating agent" as used herein includes, but is not limited to busulfan, chlorambucil, cyclophosphamide; ifosfamide, melphalan or nitrosourea (BCNU or Gliadel™).

The term "antineoplastic antimetabolite" includes, but is not limited to 5-fluorouracil, capecitabine, gemcitabine, cytarabine, fludarabine, thioguanine, methotrexate and edatrexate.

The term "platin compound" as used herein includes, but is not limited to carboplatin, cis-platin and oxaliplatin.

The term "compounds targeting/decreasing a protein or lipid kinase activity or further anti-angiogenic compounds" as used herein includes, but is not limited to protein tyrosine kinase and/or serine and/or threonine kinase inhibitors or lipid kinase inhibitors, e.g. compounds targeting, decreasing or inhibiting the activity of the epidermal growth factor family of receptor tyrosine kinases (EGFR, ErbB2, ErbB3, ErbB4 as homo- or heterodimers), the vascular endothelial growth factor family of receptor tyrosine kinases (VEGFR), the platelet-derived growth factor-receptors (PDGFR), the fibroblast growth factor-receptors (FGFR), the insulin-like growth factor receptor 1 (IGF-1R), the Trk receptor tyrosine kinase family, the Axl receptor tyrosine kinase family, the Ret receptor tyrosine kinase, the Kit/SCFR receptor tyrosine kinase, members of the c-Abl family and their gene-fusion products (e.g. BCR-Abl), members of the protein kinase C (PKC) and Raf family of serine/threonine kinases, members of the MEK, SRC, JAK, FAK, PDK or PI(3) kinase family, or of the PI(3)-kinase-related kinase family, and/or members of the cyclin-dependent kinase family (CDK) and anti-angiogenic compounds having another mechanism for their activity, e.g. unrelated to protein or lipid kinase inhibition.

Compounds which target, decrease or inhibit the activity of VEGFR are especially compounds, proteins or antibodies which inhibit the VEGF receptor tyrosine kinase, inhibit a VEGF receptor or bind to VEGF, and are in particular those compounds, proteins or monoclonal antibodies generically and specifically disclosed in WO 98/35958, e.g. 1-(4-chloroanilino)-4-(4-pyridylmethyl)phthalazine or a pharmaceutically acceptable salt thereof, e.g. the succinate, in WO 00/27820, e.g. a N-aryl(thio) anthranilic acid amide derivative e.g. 2-[(4-pyridyl)methyl]amino-N-[3-methoxy-5-(trifluoromethyl)phenyl]benzamide or 2-[(1-oxido-4-pyridyl)methyl]amino-N-[3-trifluoromethylphenyl]benzamide, or in WO 00/09495, WO 00/59509, WO 98/11223, WO 00/27819 and EP 0 769 947; those as described by M. Prewett et al in Cancer Research 59 (1999) 5209–5218, by F. Yuan et al in Proc. Natl. Acad. Sci. USA, vol. 93, pp. 14765–14770, December 1996, by Z. Zhu et al in Cancer Res. 58, 1998, 3209–3214, and by J. Mordenti et al in Toxicologic Pathology, Vol. 27, no. 1, pp 14–21, 1999; in WO 00/37502 and WO 94/10202; Angiostatin™, described by M. S. O'Reilly et al, Cell 79, 1994, 315–328; Endostatin™, described by M. S. O'Reilly et al, Cell 88, 1997, 277–285; anthranilic acid amides; ZD4190; ZD6474; SU5416; SU6668; or anti-VEGF antibodies or anti-VEGF receptor antibodies, e.g. RhuMab.

By antibody is meant intact monoclonal antibodies, polyclonal antibodies, multispecific antibodies formed from at least 2 intact antibodies, and antibody fragments so long as they exhibit the desired biological activity.

Compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, or which have a dual inhibiting effect on the ErbB and VEGF receptor kinase and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180) or PCT/EP02/08780; e.g. trastuzumab (Herpetin$^R$), cetuximab, Iressa, OSI-774, CI-1033, EKB-569, GW-2016, E1.1, E2.4, E2.5, E6.2, E6.4, E2.11, E6.3 or E7.6.3.

Compounds which target, decrease or inhibit the activity of PDGFR are especially compounds which inhibit the PDGF receptor, e.g. a N-phenyl-2-pyrimidine-amine derivative, e.g. imatinib.

Compounds which target, decrease or inhibit the activity of c-Abl family members and their gene fusion products are, e.g. a N-phenyl-2-pyrimidine-amine derivative, e.g. imatinib; PD180970; AG957; or NSC 680410.

Compounds which target, decrease or inhibit the activity of protein kinase C, Raf, MEK, SRC, JAK, FAK and PDK family members, or PI(3) kinase or PI(3) kinase-related family members, and/or members of the cyclin-dependent kinase family (CDK) are especially those staurosporine derivatives disclosed in EP 0 296 110, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; or LY333531/LY379196.

Further anti-angiogenic compounds are e.g. thalidomide (THALOMID) and TNP-470.

Compounds which target, decrease or inhibit the activity of a protein or lipid phosphatase are, e.g. inhibitors of phosphatase 1, phosphatase 2A, PTEN or CDC25, e.g. okadaic acid or a derivative thereof.

Compounds which induce cell differentiation processes are, e.g. retinoic acid, α-, γ- or δ-tocopherol or α-, γ- or δ-tocotrienol.

The term cyclooxygenase inhibitor as used herein includes, but is not limited to, e.g. celecoxib (Celebrex$^R$), rofecoxib (Vioxx$^R$), etoricoxib, valdecoxib or a 5-alkyl-2-arylaminophenylacetic acid, e.g. 5-methyl-2-(2'-chloro-6'-fluoroanilino)phenyl acetic acid. The term "histone deacetylase inhibitor" as used herein includes, but is not limited to MS-27-275, SAHA, pyroxamide, FR-901228 or valproic acid.

The term "bisphosphonates" as used herein includes, but is not limited to, etridonic, clodronic, tiludronic, pamidronic, alendronic, ibandronic, risedronic and zoledronic acid.

The term "matrix metalloproteinase inhibitor" as used herein includes, but is not limited to collagen peptidomimetic and non-petidomimetic inhibitors, tetracycline derivatives, e.g. hydroxamate peptidomimetic inhibitor batimastat and its orally bioavailable analogue marimastat, prinomastat, BMS-279251, BAY 12-9566, TAA211 or AAJ996.

The term "mTOR inhibitor" as used herein includes, but is not limited to rapamycin (sirolimus) or a derivative thereof, e.g. 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40-O-(2-hydroxyethyl)-rapamycin and, more preferably, 40-O-(2-hydroxyethyl)-rapamycin. Further examples of rapamycin derivatives include e.g. CCI779 or 40-[3-hydroxy-2-(hydroxymethyl)-2-methylpropanoate]-rapamycin or a pharmaceutically acceptable salt thereof, as disclosed in U.S. Pat. No. 5,362,718, ABT578 or 40-(tetrazolyl)-rapamycin, particularly 40-epi-(tetrazolyl)-rapamycin, e.g. as disclosed in WO 99/15530, or rapalogs as disclosed e.g. in WO 98/02441 and WO01/14387, e.g. AP23573.

Where the compounds of formula I are administered in conjunction with other immunosuppressive/immunomodulatory, anti-inflammatory or chemotherapeutic therapy, dosages of the co-administered immunosuppressant, immunomodulatory, antiinflammatory or chemotherapeutic compound will of course vary depending on the type of co-drug employed, e.g. whether it is a steroid or a calcineurin inhibitor, on the specific drug employed, on the condition being treated and so forth.

In accordance with the foregoing the present invention provides in a yet further aspect.

5. A method as defined above comprising co-administration, e.g. concomitantly or in sequence, of a therapeutically effective non-toxic amount of a compound of formula I and at least a second drug substance, e.g. an immunosuppressant, immunomodulatory, anti-inflammatory or chemotherapeutic drug, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory or chemotherapeutic drug, e.g. as disclosed above. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

In each case where citations of patent applications or scientific publications are given, the subject-matter relating to the compounds is hereby incorporated into the present application by reference. Comprised are likewise the pharmaceutically acceptable salts thereof, the corresponding racemates, diastereoisomers, enantiomers, tautomers as well as the corresponding crystal modifications of above disclosed compounds where present, e.g. solvates, hydrates and polymorphs, which are disclosed therein. The compounds used as active ingredients in the combinations of the invention can be prepared and administered as described in the cited documents, respectively. Also within the scope of this invention is the combination of more than two separate active ingredients as set forth above, i.e. a pharmaceutical combination within the scope of this invention could include three active ingredients or more. Further both the first agent and the co-agent are not the identical ingredient.

We claim:

1. A compound of formula I

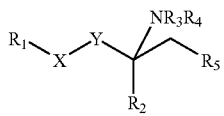

wherein

Y is —CH$_2$CH$_2$—, —CH$_2$CH(OH)—, —CH(OH)CH$_2$—, —C(O)CH$_2$—, —CH$_2$C(O)—, —CH═CH—; or 1,2-cyclopropylene;

X is phenylene optionally substituted by one to three substituents selected from halogen, nitro, C$_{1-10}$alkyl and halogen-substituted C$_{1-6}$alkyl;

R$_1$ is phenyl or phenyl-C$_{2-4}$alkenyl, each being substituted by (i) one to three substituents selected from hydrogen, halogen, amino, phenyl, heteroaryl, heteroaryl-C$_{1-4}$alkyl, C$_{1-10}$alkyl, cycloalkyl-C$_{1-4}$alkyl, cycloalkyl-C$_{1-4}$alkoxy, C$_{1-10}$alkoxy, C$_{2-10}$alkenyl, C$_{2-10}$alkynyl, C$_{1-10}$alkylthio, C$_{1-10}$alkylsulfonyl, C$_{1-10}$alkylsulfinyl, C$_{1-4}$alkyl-S(O)$_2$NH—, phenylC$_{1-6}$alkyl, or phenylC$_{1-6}$alkoxy, in each of which any aliphatic part of the group may be straight or branched chain and optionally substituted by up to three substituents selected from halogen, amino, hydroxy, cyano, or cycloalkyl groups and optionally interrupted by a double or triple bond or one or more C(O), NR$_{12}$, S, S(O), S(O)$_2$ or O groups, wherein R$_{12}$ is hydrogen or C$_{1-6}$alkyl; and any aromatic group may be optionally substituted by one to three substituents selected from halogen, cyano, amino, C$_{1-4}$alkyl halogen-substituted-C$_{1-4}$alkyl and C$_{1-8}$alkoxy; and/or (ii) a group of formula (a):

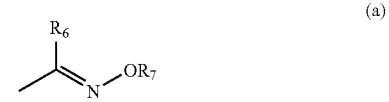

in which

R$_6$ and R$_7$, independently, is hydrogen; phenyl, C$_{1-10}$alkyl, cycloalkyl, heteroaryl, heteroaryl-C$_{1-4}$alkyl, C$_{1-10}$alkoxy, C$_{2-10}$alkenyl, C$_{2-10}$alkynyl, C$_{1-10}$alkylthio, C$_{1-10}$alkylsulfonyl, C$_{1-10}$alkylsulfinyl, phenylC$_{1-8}$alkyl, or phenylC$_{1-6}$alkoxy, in each of which any aliphatic part of the group may be straight chain or branched and may be optionally substituted by up to three halogen, hydroxy, cycloalkyl, or C$_{1-4}$alkoxy groups and optionally interrupted by a double or triple bond or one or more C(O), NR$_{12}$, S, S(O), S(O)$_2$ or O groups, and any aromatic group may be optionally substituted by one to three substituents selected from halogen, CF$_3$, C$_{1-8}$alkyl and C$_{1-8}$alkoxy;

R$_2$ is hydrogen; halogen; C$_{1-4}$alkyl optionally substituted with one or more halogens; C$_{2-6}$ alkenyl; C$_{2-6}$alkynyl; or cycloalkyl optionally substituted by halogen; aryl optionally substituted with hydroxy; or C$_{1-4}$alkyl optionally substituted on the terminal C atom by OH or a residue of formula (h):

in which Z is a direct bond, O, S, (CH$_2$)$_{1-2}$, CF$_2$, or NR$_{11}$ where R$_{11}$ is H, (C$_{1-4}$)alkyl or halogen-substituted (C$_{1-4}$)alkyl; and each of R$_9$ and R$_{10}$, independently, is H, OH, (C$_{1-4}$)alkyl optionally substituted by one to three halogens, or (C$_{1-4}$)alkoxy optionally substituted by halogen; with the proviso that R$_9$ and R$_{10}$ are not both hydrogen;

each of R$_3$ and R$_4$, independently, is H or C$_{1-4}$alkyl optionally substituted by halogen or acyl; and R$_5$ is H, —OH, —Oacyl, —NHacyl, or a residue of formula (h) as defined above;

provided that at least either R$_2$ comprises a terminal OH or a residue of formula (h) or R$_5$ is OH or a residue of formula (h), or a salt thereof.

2. A compound according to claim 1, wherein X is 1,4-phenylene, Y is —CH$_2$—CH$_2$—, R$_1$ is phenyl monosubstituted in position para by a group R$_{15}$ wherein R$_{15}$ is straight chain C$_{5-8}$alkyl; C$_{2-8}$alkenyl; or straight chain or branched C$_{1-8}$alkoxy optionally substituted by one C$_{3-6}$cycloalkyl or by a phenyl group optionally substituted by up to three halogens; or R$_1$ is para-monosubstituted phenyl substituted by a group of formula (a), as defined in claim 1, R$_2$ is C$_{1-4}$alkyl optionally substituted on the terminal C atom by OH or a residue of formula (h) as defined above, R$_3$ and R$_4$ are hydrogen, and R$_5$ is OH, or a salt thereof.

3. A compound according to claim 1 or 2, wherein $R_1$ is phenyl monosubstituted in position para by a group of formula (a) as defined above, or a salt thereof.

4. A compound according to claim 1, wherein Z is O, or a salt thereof.

5. A process for preparing a compound according to claim 1 which process comprises removing the hydrolysable groups present in a compound of formula II

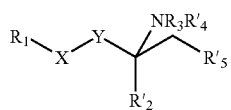

I wherein X, Y, $R_1$ and $R_3$ are as defined in claim 1, $R_4'$ is an amino protecting group, $R_2'$ has one of the significances given for $R_2$ above except that the terminal OH when present in the OH-substituted $C_{1-4}$alkyl is in protected form or the residue of formula (h) is replaced by a residue of formula (h') and $R_5'$ is $R_5''$ in which $R_5''$ is H, —OH in protected form or a residue of formula (h'), provided that at least one of $R_2'$ and $R_5'$ is OH in protected form or a residue of formula (h'), the residue of formula (h') being:

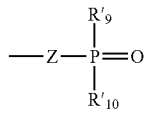

(h')

wherein Z is as described above, and each of $R_9'$ and $R_{10}'$ is a hydrolysable group and, where required, converting the compounds of formula I obtained in free form into the desired salt form, or vice versa.

6. A pharmaceutical composition comprising a compound of claim 1, or a pharmaceutically acceptable salt thereof in association with a pharmaceutically acceptable diluent or carrier therefor.

7. A method for treating acute or chronic transplant rejection in a subject comprising administering to the subject in need thereof an effective amount of a compound of claim 1, or a pharmaceutically acceptable salt thereof.

* * * * *